United States Patent
Bienvenu et al.

(10) Patent No.: US 9,867,724 B2
(45) Date of Patent: *Jan. 16, 2018

(54) HOLLOW DRUG-FILLED STENT AND METHOD OF FORMING HOLLOW DRUG-FILLED STENT

(71) Applicant: Medtronic Vascular, Inc., Santa Rosa, CA (US)

(72) Inventors: Ryan Bienvenu, Santa Rosa, CA (US); James Mitchell, Windsor, CA (US); Dustin Thompson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 150 days.

This patent is subject to a terminal disclaimer.

(21) Appl. No.: 14/636,371

(22) Filed: Mar. 3, 2015

(65) Prior Publication Data

US 2015/0245930 A1    Sep. 3, 2015

Related U.S. Application Data

(63) Continuation of application No. 13/447,004, filed on Apr. 13, 2012, now Pat. No. 8,998,977.

(51) Int. Cl.
*A61F 2/86* (2013.01)
*A61L 31/16* (2006.01)
(Continued)

(52) U.S. Cl.
CPC ............... *A61F 2/86* (2013.01); *A61F 2/91* (2013.01); *A61L 31/022* (2013.01); *A61L 31/16* (2013.01);
(Continued)

(58) Field of Classification Search
CPC .... A61F 2/856; A61F 2/86; A61F 2/88; A61F 2/91; A61F 2240/001; A61F 2250/0068;
(Continued)

(56) References Cited

U.S. PATENT DOCUMENTS

| 4,800,882 A | 1/1989 | Gianturco |
| 4,886,062 A | 12/1989 | Wikto |

(Continued)

FOREIGN PATENT DOCUMENTS

| EP | 0916362 | 3/1998 |
| EP | 0875218 | 8/2000 |

(Continued)

*Primary Examiner* — Edward Tolan

(57) ABSTRACT

A stent is formed from a wire having an outer member, a radiopaque member lining at least a portion of the outer member inner surface, and a lumen defined by the outer member inner surface or the radiopaque member inner surface. A substance is disposed in the lumen to be eluted through at least one opening disposed through the outer member to the lumen. The radiopaque member may be substantially continuous along the length of the wire or disposed only along portions of the wire such as crowns. In a method for making the stent, a composite wire including an outer member, a radiopaque intermediate member, and a core member is shaped into a stent pattern and processed to remove the core member and optionally portions of the radiopaque intermediate member, without damaging the outer member.

12 Claims, 14 Drawing Sheets

(51) Int. Cl.
*A61F 2/91* (2013.01)
*A61L 31/02* (2006.01)
*A61L 31/18* (2006.01)

(52) U.S. Cl.
CPC ....... *A61L 31/18* (2013.01); *A61F 2210/0076* (2013.01); *A61F 2240/001* (2013.01); *A61F 2250/0068* (2013.01); *A61F 2250/0098* (2013.01); *Y10T 29/4998* (2015.01); *Y10T 29/49817* (2015.01)

(58) Field of Classification Search
CPC ... A61F 2250/0098; A61L 31/18; A61L 31/16
See application file for complete search history.

(56) References Cited

U.S. PATENT DOCUMENTS

| | | | |
|---|---|---|---|
| 5,019,090 A | 5/1991 | Pinchuk | |
| 5,020,214 A * | 6/1991 | Tsuruoka | G01F 1/68 29/611 |
| 5,133,732 A | 7/1992 | Wiktor | |
| 5,234,456 A | 8/1993 | Silvestrini | |
| 5,370,681 A | 12/1994 | Herweck et al. | |
| 5,411,550 A | 5/1995 | Herweck et al. | |
| 5,630,840 A | 5/1997 | Mayer | |
| 5,707,385 A | 1/1998 | Williams | |
| 5,782,903 A | 7/1998 | Wiktor | |
| 5,873,904 A * | 2/1999 | Ragheb | A61F 2/82 604/265 |
| 5,891,108 A * | 4/1999 | Leone | A61F 2/88 604/264 |
| 5,954,743 A | 9/1999 | Jang | |
| 6,063,101 A | 5/2000 | Jacobsen et al. | |
| 6,071,305 A | 6/2000 | Brown et al. | |
| 6,096,070 A | 8/2000 | Ragheb et al. | |
| 6,136,023 A | 10/2000 | Boyle | |
| 6,203,732 B1 * | 3/2001 | Clubb | A61F 2/91 164/464 |
| 6,206,915 B1 * | 3/2001 | Fagan | A61F 2/07 623/1.15 |
| 6,248,190 B1 | 6/2001 | Stinson | |
| 6,254,632 B1 | 7/2001 | Wu et al. | |
| 6,364,902 B1 * | 4/2002 | Dickenson | A61F 2/91 623/1.15 |
| 6,471,721 B1 * | 10/2002 | Dang | A61F 2/91 623/1.15 |
| 6,497,709 B1 | 12/2002 | Heath | |
| 7,020,947 B2 * | 4/2006 | Bradley | B21C 1/003 29/458 |
| 7,101,392 B2 | 9/2006 | Heath | |
| 8,278,222 B2 * | 10/2012 | Wu | B08B 7/0035 438/706 |
| 8,998,977 B2 * | 4/2015 | Bienvenu | A61L 31/16 623/1.15 |
| 9,649,208 B2 * | 5/2017 | Bienvenu | A61F 2/86 |
| 2001/0001834 A1 | 5/2001 | Palmaz et al. | |
| 2001/0027340 A1 | 10/2001 | Wright et al. | |
| 2002/0040239 A1 | 4/2002 | Murayama et al. | |
| 2003/0208256 A1 | 11/2003 | DiMatteo et al. | |
| 2007/0038290 A1 | 2/2007 | Huang et al. | |
| 2010/0269950 A1 | 10/2010 | Hoff et al. | |
| 2011/0008405 A1 | 1/2011 | Birdsall et al. | |
| 2011/0070357 A1 | 3/2011 | Mitchell et al. | |
| 2011/0070358 A1 | 3/2011 | Mauch et al. | |
| 2012/0067008 A1 | 3/2012 | Bienvenu et al. | |
| 2012/0067103 A1 | 3/2012 | Bienvenu et al. | |

FOREIGN PATENT DOCUMENTS

| | | |
|---|---|---|
| WO | WO97/46268 | 12/1997 |
| WO | WO00/18327 | 4/2000 |
| WO | WO00/72907 | 12/2000 |
| WO | WO00/74584 | 12/2000 |
| WO | WO01/12158 | 2/2001 |
| WO | WO01/17577 | 3/2001 |
| WO | WO01/66036 | 9/2001 |
| WO | WO01/93781 | 12/2001 |
| WO | WO02/32347 | 4/2002 |

* cited by examiner

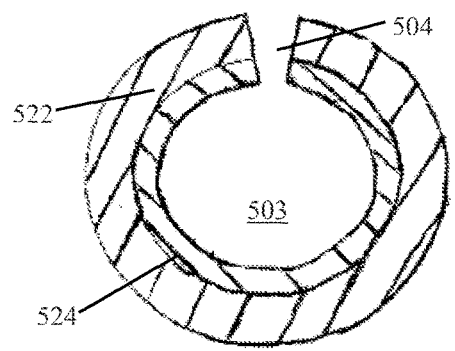
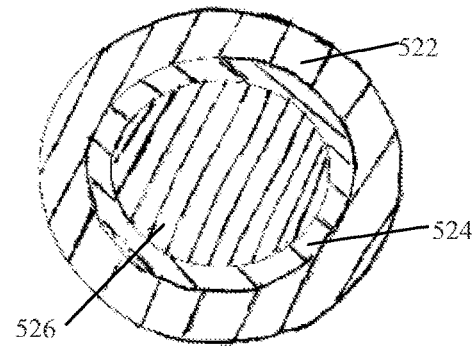
FIG. 28  FIG. 29
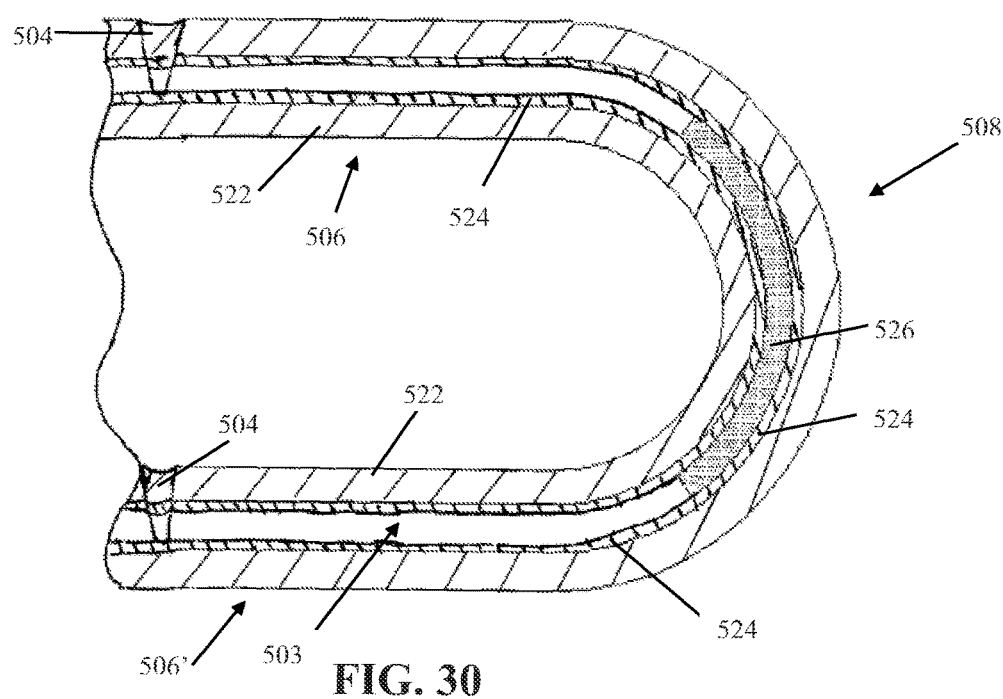
FIG. 30

HOLLOW DRUG-FILLED STENT AND METHOD OF FORMING HOLLOW DRUG-FILLED STENT

FIELD OF THE INVENTION

The present invention relates hollow drug-filled stents and methods of forming hollow-drug-filled stents, and in particular, hollow-drug filled stents with improved radiopacity.

BACKGROUND OF THE INVENTION

Drug-eluting implantable medical devices such as stents have become popular in recent times for their ability to perform their primary function (such as structural support) and their ability to medically treat the area in which they are implanted.

For example, drug-eluting stents have been used to prevent restenosis in coronary arteries. Drug-eluting stents may administer biologically or pharmacologically active substances such as anti-inflammatory compounds that block local invasion/activation of monocytes, thus preventing the secretion of growth factors that may trigger VSMC proliferation and migration. Other potentially anti-restenotic compounds include anti-proliferative agents, such as chemotherapeutics, which include rapamycin and paclitaxel. Other classes of drugs such as anti-thrombotics, anti-oxidants, platelet aggregation inhibitors and cytostatic agents have also been suggested for anti-restenotic use.

Drug-eluting medical devices may be coated with a polymeric material which, in turn, is impregnated with a biologically or pharmacologically active substance or a combination of biologically or pharmacologically active substances. Once the medical device is implanted at a target location, the biologically or pharmacologically active substance is released from the polymer for treatment of the local tissues. The biologically or pharmacologically active substance is released by a process of diffusion through the polymer layer for biostable polymers, and/or as the polymer material degrades for biodegradable polymers.

Controlling the rate of elution of a biologically or pharmacologically active substance from the impregnated polymeric material is generally based on the properties of the polymer material. However, at the conclusion of the elution process, the remaining polymer material in some instances has been linked to an adverse reaction with the vessel, possibly causing a small but dangerous clot to form. Further, drug impregnated polymer coatings on exposed surfaces of medical devices may flake off or otherwise be damaged during delivery, thereby preventing the biologically or pharmacologically active substance from reaching the target site. Still further, drug impregnated polymer coatings are limited in the quantity of the biologically or pharmacologically active substance to be delivered by the amount of a drug that the polymer coating can carry and the size of the medical devices. Controlling the rate of elution using polymer coatings is also difficult.

Accordingly, stents with hollow, drug-filled structural members have also been contemplated. For example, U.S. Pat. No. 6,071,305 to Brown et al. generally discloses a stent formed of an elongated member in a spiral tube configuration. The elongated member includes a groove that can be filled with an active agent. Further, U.S. Application Publication No. 2011/0008405 to Birdsall et al. and U.S. Application Publication No. 2011/0070358 to Mauch et al., each of which is incorporated by reference herein in its entirety, describe methods of forming stents with hollow-drug-filled structural members from composite wires. However, preferred structural members for stents, such as nickel-titanium alloys ("nitinol") and alloys of cobalt, nickel, chromium and molybdenum ("MP35N", "MP20N") are relatively radiolucent. Thus, there is a need for a stent with hollow-drug filled structural members with improved radiopacity.

SUMMARY OF INVENTION

Embodiments hereof relate to a stent formed from a wire shaped into a stent pattern. The wire includes an outer member having an outer member outer surface and an outer member inner surface and a radiopaque member lining at least a portion of the outer member inner surface. A lumen is defined by the outer member inner surface or the radiopaque member inner surface. A biologically or pharmacologically active substance disposed in the lumen. At least one opening disposed through the outer member to the lumen or through the outer member and the radiopaque member to the lumen such that the biologically or pharmacologically active substance may be eluted from the stent. In one embodiment, the stent pattern may include a series of struts connected by crowns, and the radiopaque member may line the outer member inner surface only in the crowns of the stent. In another embodiment, the radiopaque member is substantially continuous along the length of the stent.

Embodiments hereof also relate to a method of forming such a stent. A composite wire including an outer member, a radiopaque intermediate member, and a core member is shaped into a stent pattern. The composite wire is processed such that the core member is removed without adversely affecting the outer member, thereby leaving an outer member, the radiopaque intermediate member lining at least a portion of an inner surface of the outer member, and a lumen defined by a space formerly occupied by the core member. The process for removing that core member may also remove portions of the radiopaque intermediate member. Openings are formed through at least the outer member such that the openings extend to the lumen. At least a portion of the lumen is filled with a biologically or pharmacologically active substance. In one embodiment, the composite wire is shaped into a waveform including struts and crowns, and the process for removing the core member also removes portions of the radiopaque intermediate member from the struts of the waveform, thereby leaving the radiopaque intermediate member in the crowns of the waveform. In another embodiment, the process for removing the core member does not adversely affect the radiopaque intermediate member, thereby leaving the radiopaque intermediate member substantially continuous along the length of the wire (the radiopaque intermediate member may be removed at locations of openings, for example, and still be substantially continuous).

Embodiments hereof also relate to a stent including a wire formed into a stent pattern. The wire includes an outer member, a radiopaque core member disposed within at least a portion of the outer member, wherein an outer dimension of the radiopaque core member is smaller than an inner dimension of the outer member such that an annular lumen is defined between an outer surface of the radiopaque core member and an inner surface of the outer member. A biologically or pharmacologically active substance disposed in the annular lumen, and at least one opening disposed through the outer member. In one embodiment, a plurality of radiopaque core members are disposed within portions of the outer member and are separated by lumens defined by the inner surface of the outer member. The lumens and annular lumens between an outer surface of the radiopaque core member and the inner surface of the outer member are in fluid communication with each other.

Embodiments hereof also relate to a method of making such a stent. A composite wire is shaped into a stent pattern. The composite wire includes an outer member, an intermediate member, and a radiopaque core member. The composite wire is processed such that the core member is removed from portions of the composite wire without adversely affecting the outer member. The composite wire is also processed such that the intermediate member is removed, thereby leaving the outer member and lumens defined by an outer member inner surface in portions where the radiopaque core member is removed, and the outer member, radiopaque core member, and annular lumens defined between a radiopaque core member outer surface and the outer member in surface in areas where the radiopaque core member is not removed. A biologically or pharmacologically active substance is deposited in the lumens and annular lumens. Openings are provided through the outer member such that the biologically or pharmacologically active substance can be eluted from the lumens. The steps of processing the composite wire to remove portions of the radiopaque core member and processing the composite wire to remove the intermediate member can be separate steps, or can be combined where the process removes the intermediate member at a faster rate than the radiopaque core member.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 24-33 are cross-sectional and partial longitudinal cross-sectional views of the composite wire at various stages of the method of FIG. 23.

DETAILED DESCRIPTION OF THE INVENTION

Figure 1:
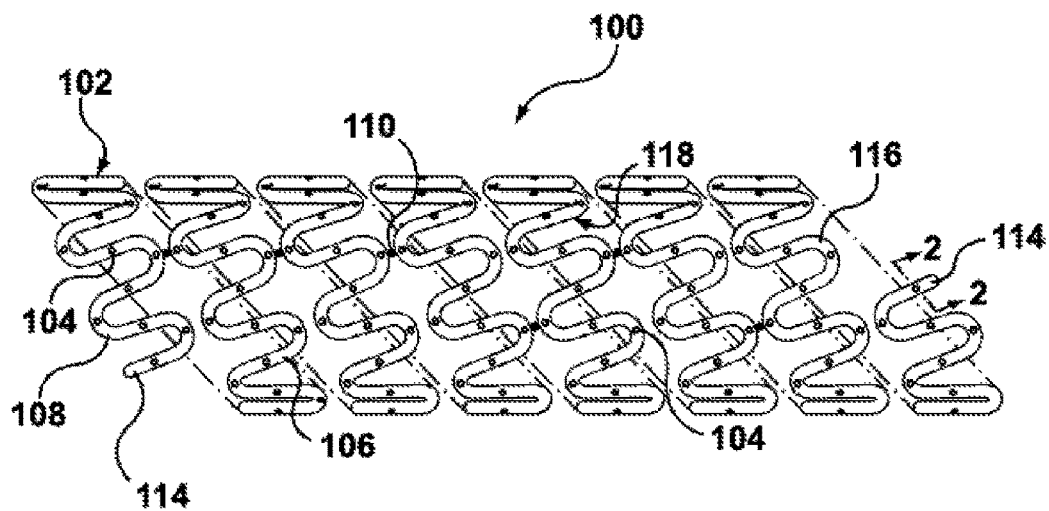
FIG. 1 is a schematic illustration of an exemplary stent in accordance with an embodiment hereof.
Figure 2:
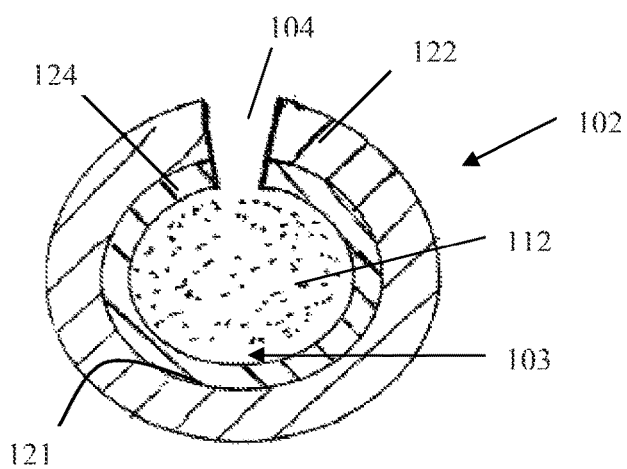
FIG. 2 is a cross-sectional view taken along line 2-2 of FIG. 1.

Specific embodiments of the present invention are now described with reference to the figures, where like reference numbers indicate identical or functionally similar elements. An embodiment of a stent 100 disclosed herein is shown in FIGS. 1-2. In particular, stent 100 is formed from a hollow wire 102, wherein the hollow wire 102 is formed of a hollow outer member 122 and a hollow intermediate member 124 that lines the inner surface 121 of outer member 122, with a lumen 103 formed within the outer and intermediate members 122, 124. The term "wire" as used herein means an elongated element or filament or group of elongated elements or filaments and is not limited to a particular cross-sectional shape or material, unless so specified. In the embodiment shown in FIG. 1, hollow wire 102 is formed into a series of generally sinusoidal waveforms including generally straight segments or struts 106 joined by bent segments or crowns 108 and the waveform is helically wound to form a generally tubular stent 100. In the embodiment shown in FIG. 1, selected crowns 108 of longitudinally adjacent sinusoids may be joined by, for example, fusion points 110. The invention hereof is not limited to the pattern shown in FIG. 1. Wire 102 of stent 100 can be formed into any pattern suitable for use as a stent. For example, and not by way of limitation, wire 102 of stent 100 can be formed into patterns disclosed in U.S. Pat. No. 4,800,882 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

As shown in FIG. 2, hollow wire 102 of stent 100 includes a hollow radiopaque intermediate member 124 that has an outer diameter that is approximately equal to the inner diameter of hollow outer member 122. By "approximately equal" it is meant that the outer surface of intermediate member 124 is in contact with the inner surface of outer member 122. Lumen 103 is formed from the hollow portion of radiopaque intermediate member 124 and the hollow portion of outer member 122 that is not occupied by radiopaque intermediate member 124. Radiopaque intermediate member 124 allows stent 100 to be visible under X-ray or fluoroscopic imaging equipment when outer member 122, described below, is made of a material that has a radiopacity such that it has poor visibility or is difficult to visualize under X-ray or fluoroscopic imaging equipment. Thus, radiopaque intermediate member 124 is more radiopaque than outer member 122. The term "radiopaque" refers to the ability of a substance to absorb X-rays. Few substances will transmit 100% of X-rays and few substances will absorb 100% of X-rays. For the purposes of this disclosure, radiopaque will refer to those substances or materials which have suitable visibility for stent procedures when being imaged by an X-ray imaging device such as but not limited to a fluoroscope.

Lumen 103 allows for a biologically or pharmacologically active substance 112 to be deposited therewithin. Although hollow wire 102 is shown as generally having a circular cross-section, hollow wire 102 may be generally elliptical or rectangular in cross-section. Hollow wire 102 further includes cuts or openings 104 dispersed along its length to provide access to lumen 103 to permit biologically or pharmacologically active substance 112 to be released from lumen 103. Openings 104 may be disposed only on struts 106 of stent 100, only on crowns 108 of stent 100, or both struts 106 and crowns 108. Openings 104 may be sized and shaped as desired to control the elution rate of biologically or pharmacologically active substance 112 from stent 100. Larger sized openings 104 generally permit a faster elution rate and smaller sized openings 104 generally provide a slower elution rate. Further, the size and/or quantity of openings 104 may be varied along stent 100 in order to vary the quantity and/or rate of biologically or pharmacologically active substance 112 being eluted from stent 100 at different portions of stent 100. Openings 104 may be, for example and not by way of limitation, 5-30 µm in diameter. Openings 104 may be provided on an outwardly facing or abluminal surface 116 of stent 100, as shown in FIG. 1, or on the inwardly facing or luminal surface 118 of stent 100, or may be provided anywhere along the circumference of wire 102. Openings 104 may have a constant diameter through the depth or have a tapered or conical shape.

Ends 114 of wire 102 may be closed. Ends 114 may be closed by crimping excess material of wire 102 to close lumen 103. Ends 114 may also be closed by not removing intermediate member 124 and core member 126, described in more detail below, from the ends 114. Closing ends 114 prevents biologically or pharmacologically active substance 112 from prematurely releasing from ends 114. However, closing ends 114 is not required as substance 112 may be dried, provided within a polymer matrix, enclosed within a liner (not shown), or otherwise protected from premature release from ends 114. Further, ends 114 may be welded, crimped or otherwise connected to other portions of wire 102 such that the ends 114 are not free ends. Ends 114 may alternatively be provided as free ends.

Figure 3:
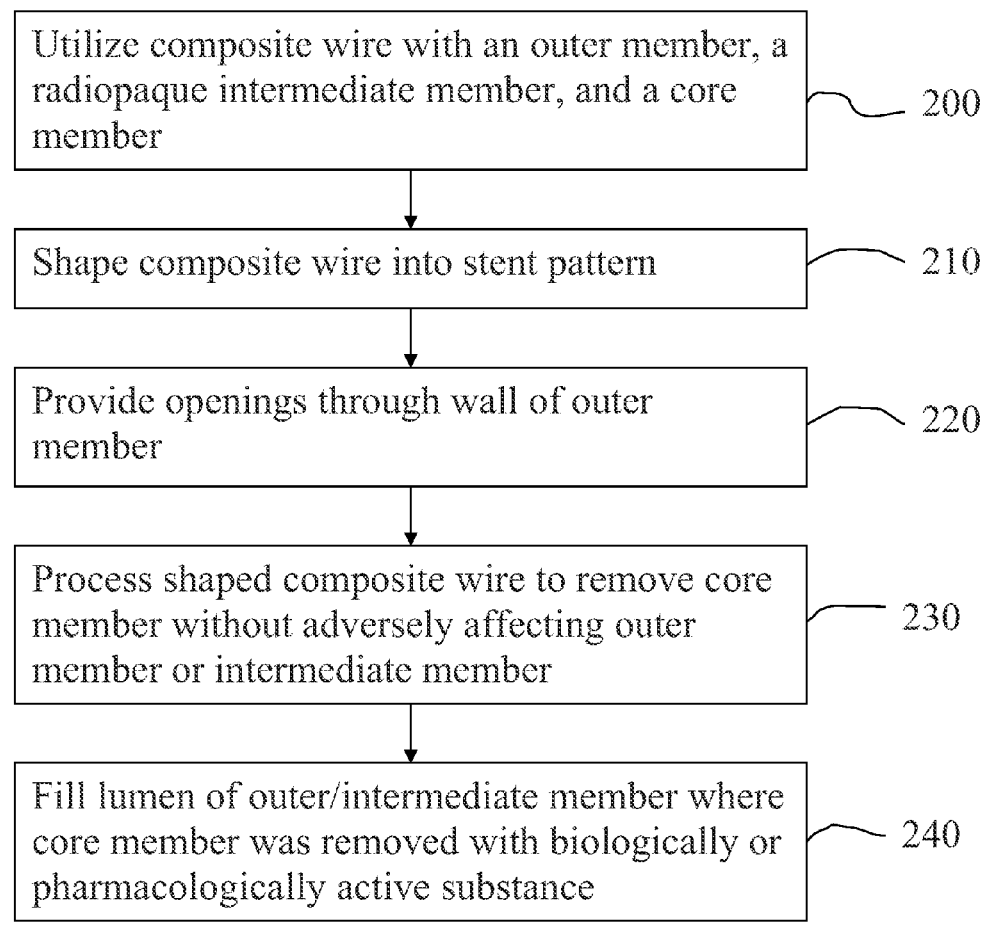
FIG. 3 is flow chart illustrating an embodiment of a method of forming a hollow wire stent including a radiopaque intermediate member disposed on an inner surface of a hollow outer member and a biologically or pharmacologically active substance disposed within a lumen of the hollow wire.

FIGS. 3-7 show a method for forming a hollow wire stent in accordance with an embodiment hereof. As shown in FIG. 3, step 200 is to utilize a composite wire 120 having an outer member 122, a radiopaque intermediate member 124, and a core member 126, as shown schematically in FIG. 4. Outer member 122 and radiopaque intermediate member 124 become hollow wire 102 of stent 100 described above after processing described below. Composite wire 120 may be formed by any method known in the art, for example and not by way of limitation, a co-drawing process, extrusion, cladding, or any other suitable method. Composite wire 120 may be formed by methods of forming composite wires known to those skilled in the art. Examples of composite wires and methods of forming composite wires can be found in U.S. Pat. No. 5,630,840 to Mayer, U.S. Pat. No. 6,248,190 to Stinson, U.S. Pat. No. 6,497,709 to Heath, and U.S. Pat. No. 7,101,392 to Heath, each of which is incorporated by reference herein in its entirety.

Outer member 122 may be any material that is suitable to be used as a stent, provided that it survives the process of removing core member 126, as described in more detail below. For example and not by way of limitation, outer member 122 may be a stainless steel, cobalt-chromium alloys, nickel titanium alloys such as Nitinol, magnesium, or combinations thereof. The term "cobalt-chromium" alloys as used herein includes alloys with cobalt and chromium. Generally, materials such as, but not limited to, cobalt-nickel-chromium alloys ("MP35N" and "MP20N") and chromium-nickel-tungsten-cobalt alloys ("L605") and cobalt-chromium-nickel-molybdenum alloys ("ELGILOY") are the types of materials included in the term "cobalt-chromium alloys" as used herein. The requirements for the material of outer member 122 are that it be biocompatible, sufficiently resilient to be used as a stent, and that it survives the process for eliminating core member 126, as discussed in more detail below.

Intermediate member 124 is a radiopaque material. Further, intermediate member 124 is a material that survives the process of eliminating core member 126, as described in detail below. Accordingly, intermediate member 124 is more radiopaque that outer member 122 and survives the process of eliminating core member 126. Thus, selection of intermediate member 124 depends on the material of core member 126 and the process selected for removing core member 126. Core member 126 is a sacrificial material that is removed without damaging intermediate member 124 or outer member 122. In a non-limiting example, outer member 122 is made of MP35N, intermediate member 124 is made of platinum-iridium alloy such as Pt10Ir or Pt20Ir, and core member 126 is made of tantalum, and the process to remove core member 126 is exposing core member 126 to xenon difluoride gas ($XeF_2$) gas at low pressure (1-6 Torr) and relatively high temperature (approximately 150° C.). Pt10Ir is a platinum-iridium alloy containing about 90% platinum by weight and about 10% iridium by weight. Similarly, Pt20Ir is a platinum-iridium alloy containing about 80% platinum by weight and about 20% iridium by weight. Other examples of material combinations of outer member 122, intermediate member 124, core member 126, and the removal method are provided below in chart form.

Figure 5:
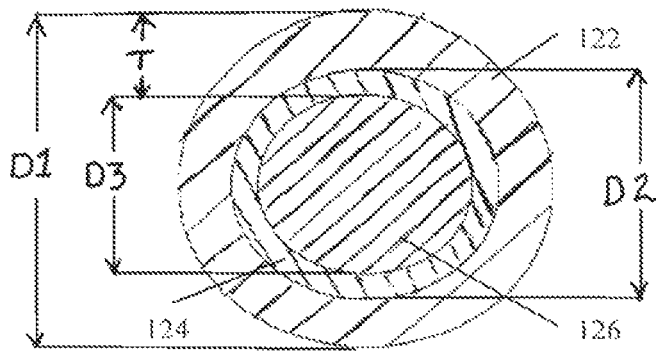
FIGS. 5-7 are cross-sectional views of the composite wire of FIG. 4 at various stages of the method of FIG. 3.

A cross-section of composite wire 120 is shown in FIG. 5. Outer member 122 may have an outer diameter D1 in the range of 0.0017 inch to 0.016 inch and wall thickness T in the range of 0.0005 to 0.0025 inch, depending on the application, for example, in what lumen or organ and for what purpose the stent is to be utilized. Intermediate member 124 may have an inner diameter of about 0.0005 to 0.006 inch and a thickness in the range of about 0.0001 to about 0.0025 inch. Core member 126 may have a diameter of about 0.0005 to about 0.006 inch. In one non-limiting example, core member 126 has a diameter of 0.001 inch, intermediate member 124 has a wall thickness of 0.0005 inch, and outer member 122 has a wall thickness of 0.00075 inch, resulting in an outer diameter D1 of core wire 120 0.0035 inch. The values listed above are merely examples and other diameters and thicknesses may be used depending on, for example, the materials used, the desired stent shape, and the purpose or location of the stent. Further, although the dimensions listed are described as diameters, other shapes of wire may be utilized and the values listed above can be converted to outer and inner dimensions.

Referring back to FIG. 3, step 210 is to shape the composite wire 120 into the stent pattern. As discussed above, the stent pattern can be the pattern shown in FIG. 1 or any other suitable pattern formed from a wire. Further, although the order of all the steps is not critical, step 210 should be done prior to removing core member 126, as explained in more detail below. However, the step of shaping the composite member 120 into the stent pattern does not have to include shaping composite member 120 into the final stent pattern. For example, the step 210 of shaping the composite member 120 into a stent pattern may include only forming the struts 106 and crowns 108 in composite wire 120. Shaping composite wire 120 into the stent pattern while core member 126 and intermediate member 124 are disposed within outer member 122 helps prevent kinking or other deformations from occurring in outer member 122. Shaping the composite wire 120 into the stent pattern shown in FIG. 1 generally includes the steps of forming composite wire 120 into a two dimensional waveform pattern followed by wrapping the pattern around a mandrel, as known to those skilled in the art. The end result is a helical stent pattern formed onto a mandrel. Selected crowns 108 of the helical pattern may then be fused together and the stent may be removed from the mandrel. Step 210 of shaping composite wire 120 into the stent pattern can be performed with techniques known to those skilled in the art. For example, and not by way of limitation, forming the composite wire 120 into a two dimensional waveform can be achieved using techniques described in U.S. Application Publication Nos. 2010/0269950 to Hoff et al. and 2011/0070358 to Mauch et al., and co-pending U.S. application Ser. Nos. 13/191,134 and 13/190,775, filed Jul. 26, 2011, each of which is incorporated in its entirety by reference herein. Other techniques known to those skilled in the art could also be used.

Figure 6:
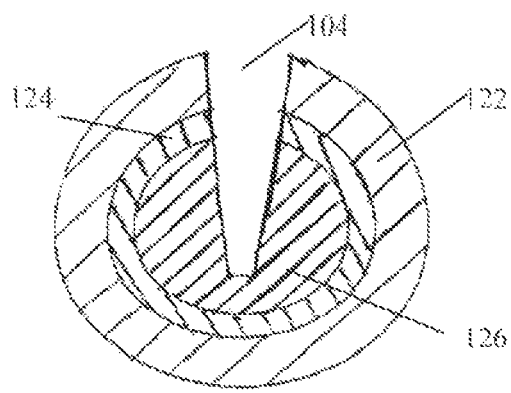
Figure 7:
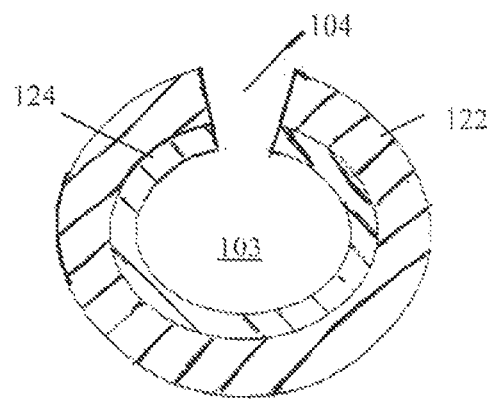

Step 220 shown in FIG. 3 is to provide openings 104 through outer member 122 and intermediate member 124. Openings 104 may be laser cut, drilled, etched, or otherwise provided through outer member 122 and intermediate member 124. Step 220 need not be performed after step 210, nor before step 230, although it is preferred to be before step 230, as explained in more detail below. If step 220 is performed after step 210, a cross-section of composite wire 120 will include outer member 122, intermediate member 124, core member 126, and an opening 104, as shown in FIG. 6.

Step 230 is to remove core member 126 from lumen 103 of outer member 122 and intermediate member 124 without adversely affecting outer member 122 or intermediate member 124, such as by chemical etching. Step 230 can be performed by any suitable process for removing core member 126 while preserving outer member 122 and intermediate member 124. In particular, exposing composite wire 120 formed from a outer member 122 of MP35N, an intermediate member 124 of a platinum-iridium alloy (such as PT10Ir or Pt20Ir), and a core member 126 of tantalum to xenon difluoride ($XeF_2$) gas at low pressure (1-6 Torr) and relatively high temperature (approximately 150° C.) causes the xenon difluoride ($XeF_2$) gas to react with the tantalum core member 126 to form $TaF_5$ and Xe gases, which can be exhausted from lumen 103. Xenon difluoride ($XeF_2$) gas reacts similarly with a core member 126 made from tungsten, molybdenum, niobium, rhenium, carbon, germanium, and silicon. However, xenon difluoride ($XeF_2$) gas does not react with an outer member 102 formed of MP35N or an intermediate member 124 formed of platinum-iridium alloys such as Pt20Ir and Pt10Ir described above. Accordingly, after step 230 is completed, outer member 122 and intermediate member 124 remain, and core member 126 has been removed, leaving the cross-sectional structure shown in FIG. 7. As noted above, openings 104 do not need to be formed prior to the step of removing core member 126 as long as there is a way to expose core member 126 to the etchant. For example, ends 114 of the wire may be open or temporary ports may for formed through outer member 122 and intermediate member 124 to expose core member 126 to the etchant.

Although a particular embodiment of an outer member 122 made from MP35N, an intermediate member 124 made from a platinum iridium alloy, a core member 126 made from tantalum, and a xenon difluoride etchant has been described, those skilled in the art would recognize other combinations of materials and etchants that could be utilized. For example, and not by way of limitation, the combination of materials and etchants described in the chart below may be utilized.

| Etchant | Outer Member | Intermediate Member | Core Member |
|---|---|---|---|
| Xenon-difluoride | Cobalt-chromium alloys (MP35N, MP20N, L605, ELGILOY) | Pt20Ir, Pt10Ir | Tantalum, tungsten, molybdenum, niobium, rhenium, carbon, germanium, silicon, Ta-2.5W |
| Nitric Acid, sulfuric acid | Cobalt-chromium alloys (MP35N, MP20N, L605, ELGILOY), Nitinol, Titanium, Titanium alloys | Tantalum, Ta-2.5W | Copper |
| Nitric Acid | Cobalt-chromium alloys (MP35N, MP20N, L605, ELGILOY), Nitinol, Titanium, Titanium alloys | Tantalum, Ta-2.5W | Silver |
| Water, salt water | Cobalt-chromium alloys(MP35N, MP20N, L605, ELGILOY), stainless steel, Nitinol, Titanium, Titanium alloys | Pt20Ir, Pt10Ir, Tantalum, Ta-2.5W | Zinc, Magnesium |
| Heat (separation via melt or sublimation) | Cobalt-chromium alloys(MP35N, MP20N, L605, ELGILOY), stainless steel, Nitinol, Titanium, Titanium alloys | Pt20Ir, Pt10Ir, Tantalum, Ta-2.5W | Zinc, Magnesium |
| Xenon difluoride Dilute HF | Cobalt-chromium alloys(MP35N, MP20N, L605, ELGILOY) | Pt20Ir, Pt10Ir | Titanium, Titanium alloys |

Further, other materials and methods for removing core members may be used, as described, for example, in U.S. Application Publication no. 2011/0008405 to Birdsall et al. and U.S. Application Publication No. 2011/0070358 to Mauch et al., each of which is incorporated by reference herein in its entirety.

After core member 126 has been removed, biologically or pharmacologically active substance 112 may be injected into lumen 103 of outer member 122 and intermediate member 124, as shown in step 240 of FIG. 3. This produces a hollow wire 102 with outer member 122, radiopaque intermediate member 124 lining an inside surface 121 of outer member 122, biologically or pharmacologically active substance 112 filling lumen 103, and openings 104 through which biologically or pharmacologically active substance 112 may be eluted, as shown in FIG. 2. Filling lumen 103 with a biologically or pharmacologically active substance may be accomplished by any means known to those skilled in the art. For example, and not by way of limitation, methods for filling lumens of hollow wires described in U.S. Application Publication No. 2011/0070357 to Mitchell et al., which is incorporated by reference herein in its entirety; and co-pending U.S. application Ser. Nos. 12/884,362; 12/884,451; 12/884,501; 12/884,578; 12/884,596 each filed on Sep. 17, 2010, and each of which is incorporated by reference herein in its entirety.

The biologically or pharmacologically active substance 112 may include, but is not limited to, the substances listed in this specification below, after description of FIGS. 23-33.

FIGS. 8-18 show an embodiment of a stent 300 and a method of making stent 300. In particular, stent 300 is formed from a hollow wire 302, wherein the hollow wire 302 is formed generally a hollow outer member with a lumen formed within the outer member. The term "wire" as used herein means an elongated element or filament or group of elongated elements or filaments and is not limited to a particular cross-sectional shape or material, unless so specified.

Figure 8:
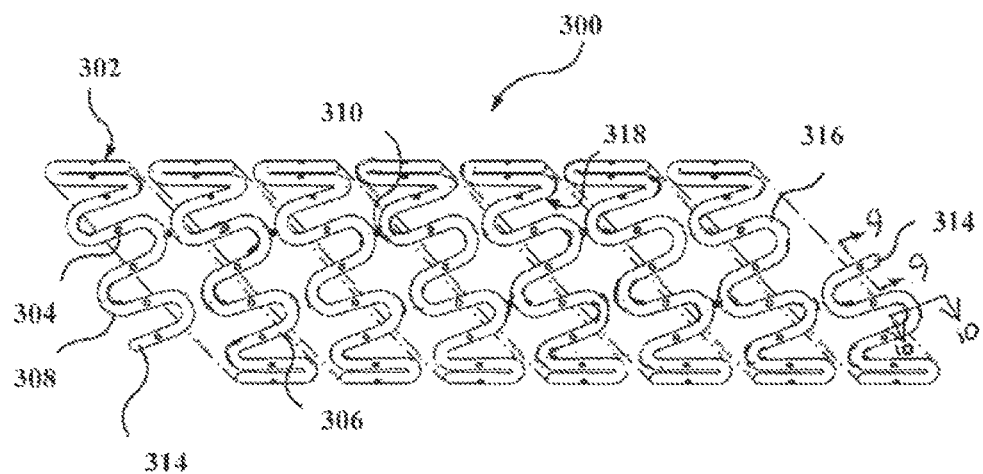
FIG. 8 is a schematic illustration of an exemplary stent in accordance with an embodiment hereof.

In the embodiment shown in FIG. 8, hollow wire 302 is formed into a series of generally sinusoidal waveforms including generally straight segments or struts 306 joined by bent segments or crowns 308 and the waveform is helically wound to form a generally tubular stent 300. In the embodiment shown in FIG. 8, selected crowns 308 of longitudinally adjacent sinusoids may be joined by, for example, fusion points 310. The invention hereof is not limited to the pattern shown in FIG. 8. Wire 302 of stent 300 can be formed into any pattern suitable for use as a stent. For example, and not by way of limitation, wire 302 of stent 300 can be formed into patterns disclosed in U.S. Pat. No. 4,800,882 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

Figures 9, 10:
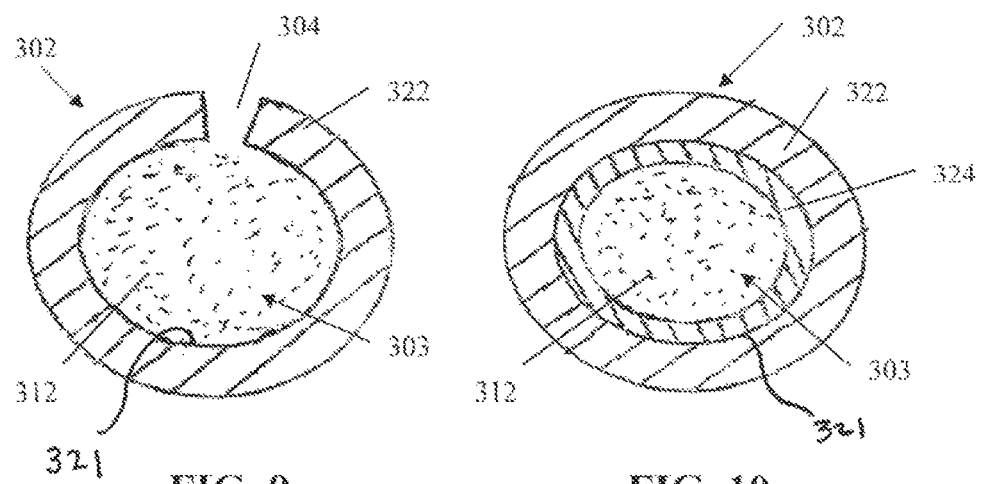
FIG. 9 is a cross-sectional view taken along line 9-9 of FIG. 8.
FIG. 10 is a cross-sectional view taken along line 10-10 of FIG. 8.
Figure 11:
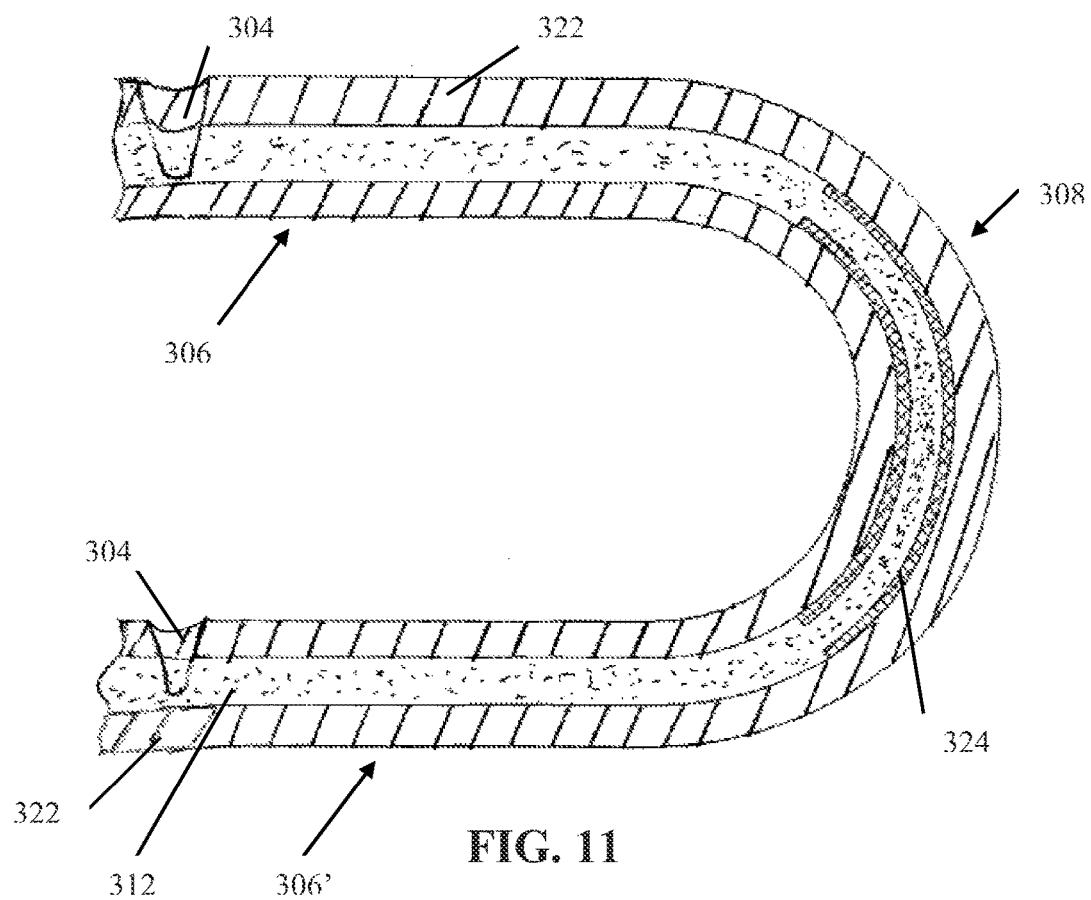
FIG. 11 is a longitudinal cross-section of a portion of the stent of FIG. 8.

As shown in FIGS. 9-11, hollow wire 302 of stent 300 includes different configurations for the struts 306 and the crowns 308. In particular, FIG. 9 shows a cross-section of wire 302 at struts 306. As can be seen in FIG. 9, wire 302 at struts 306 is formed from an outer member 322 with a lumen 303 filled with a biologically or pharmacologically active substance 312. Similarly, as shown in FIG. 10, wire 302 at crowns 308 is formed of a hollow outer member 322, a hollow radiopaque intermediate member 324 lining the inside surface 321 of outer member 322, and lumen 303 filled with biologically or pharmacologically active substance 312. FIG. 11 shows a longitudinal cross-section showing a portion of stent 300 including a strut 306, a crown 308, and a second strut 306. As shown in FIG. 11, radiopaque intermediate member 324 lines an inner surface of outer member 322 in the region of the crowns 308. The length of radiopaque intermediate member 324 may be varied such that radiopaque intermediate member 324 extends along the inner surface of outer member 322 for the entire crown 308, a portion of crown 308, or all of crown 308 and a portion of struts 306, as described in more detail below. Radiopaque intermediate member 324 should extend along crown 308 for at least a sufficient length such the radiopaque intermediate member is visible under fluoroscopic equipment. Every crown 308 of stent 300 may include radiopaque intermediate member 324 or only some crowns 308 may include radiopaque intermediate member 324. Some options of how to select whether or not some crowns 308 include or do not include radiopaque intermediate member will be described below when describing the method of forming stent 300. Hollow radiopaque intermediate member 324 has an outer diameter that is approximately equal to the inner diameter of hollow outer member 322. By "approximately equal" it is meant that the outer surface of intermediate member 324 is in contact with the inner surface 321 of outer member 322. Radiopaque intermediate member 324 allows crowns 308 of stent 300 to be visible under X-ray or fluoroscopic imaging equipment when outer member 322, described below, is made of a material that has a radiopacity such that it has poor visibility or is difficult to visualize under X-ray or fluoroscopic imaging equipment. Thus, radiopaque intermediate member 324 is more radiopaque than outer member 322. The term "radiopaque" refers to the ability of a substance to absorb X-rays. Few substances will transmit 100% of X-rays and few substances will absorb 100% of X-rays. For the purposes of this disclosure, radiopaque will refer to those substances or materials which have suitable visibility for stent procedures when being imaged by an X-ray imaging device such as but not limited to a fluoroscope.

Lumen 303 allows for a biologically or pharmacologically active substance 312 to be deposited therewithin. Although hollow wire 302 is shown as generally having a circular cross-section, hollow wire 302 may be generally elliptical or rectangular in cross-section. Hollow wire 302 further includes cuts or openings 304 dispersed along its length to provide access to lumen 303 to permit biologically or pharmacologically active substance 312 to be released from lumen 303. Openings 304 may be disposed only on struts 306 of stent 300, only on crowns 308 of stent 300, or both struts 306 and crowns 308. Openings 304 may be sized and shaped as desired to control the elution rate of biologically or pharmacologically active substance 312 from stent 300. Larger sized openings 304 generally permit a faster elution rate and smaller sized openings 304 generally provide a slower elution rate. Further, the size and/or quantity of openings 304 may be varied along stent 300 in order to vary the quantity and/or rate of biologically or pharmacologically active substance 312 being eluted from stent 300 at different portions of stent 300. Openings 304 may be, for example and not by way of limitation, 5-30 µm in diameter. Openings 304 may be provided on an outwardly facing or abluminal surface 316 of stent 100, as shown in FIG. 8, or on the inwardly facing or luminal surface 318 of stent 300, or may be provided anywhere along the circumference of wire 302. Openings 304 may have a constant diameter through the depth or have a tapered or conical shape.

Ends 314 of wire 302 may be closed. Ends 314 may be closed by crimping excess material of wire 302 to close lumen 303. Ends 314 may also be closed by not removing intermediate member 324 and core member 326, described in more detail below, from the ends 314. Closing ends 314 prevents biologically or pharmacologically active substance 312 from prematurely releasing from ends 314. However, closing ends 314 is not required as substance 312 may be dried, provided within a polymer matrix, enclosed within a liner (not shown), or otherwise protected from premature release from ends 314. Further, ends 314 may be welded, crimped or otherwise connected to other portions of wire 302 such that the ends 314 are not free ends. Ends 314 may alternatively be provided as free ends.

Figure 4:
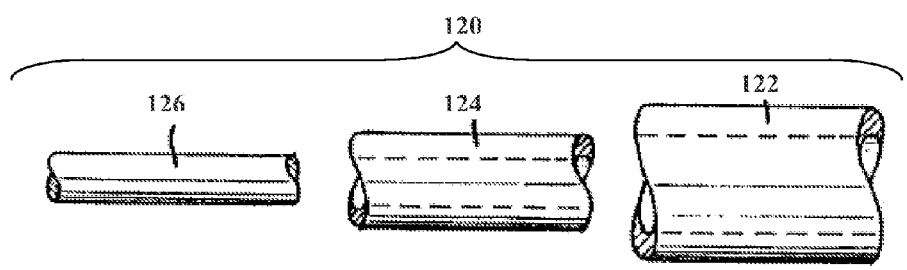
FIG. 4 is a schematic illustration of a composite wire including an outer member, an intermediate member, and a core member.
Figure 12:
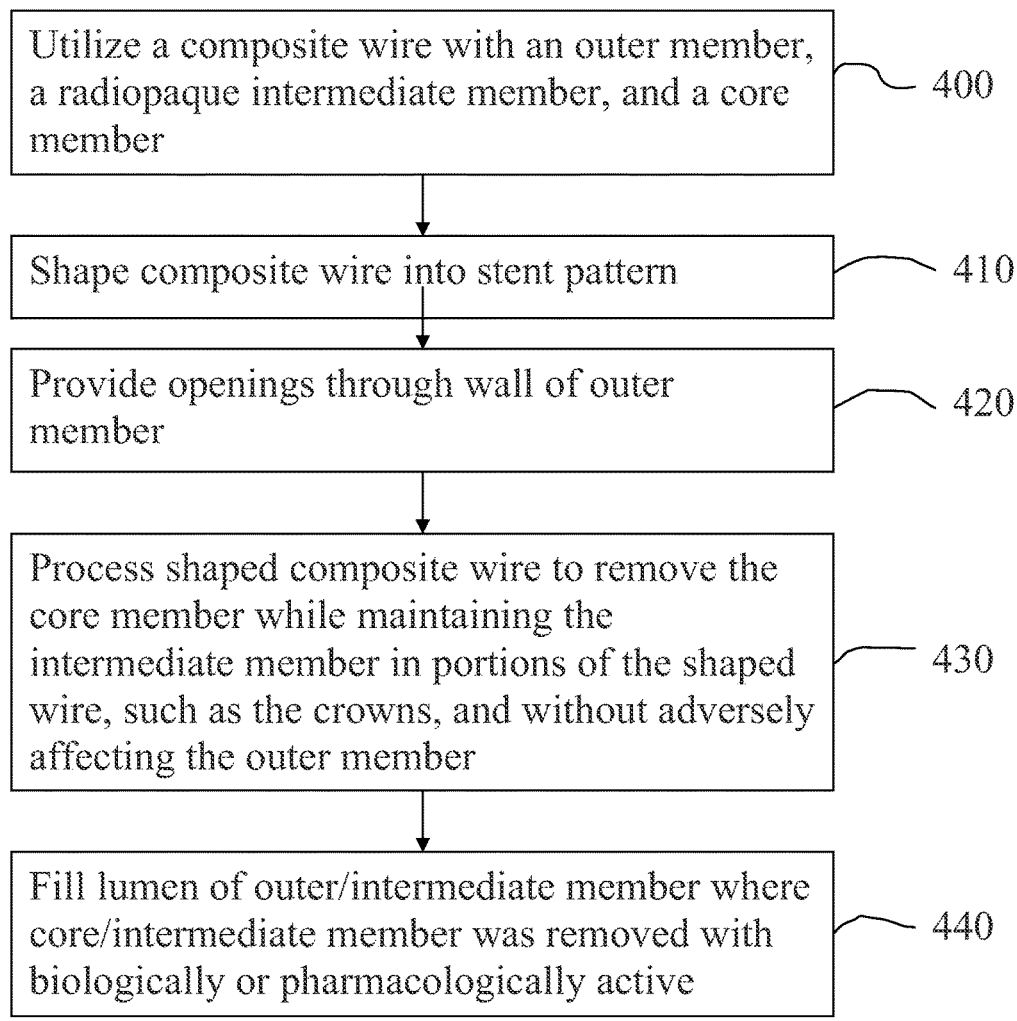
FIG. 12 is flow chart illustrating an embodiment of a method of forming a hollow wire stent including a radiopaque intermediate member disposed on an inner surface of a hollow outer member at the crowns of the stent and a biologically or pharmacologically active substance disposed within a lumen of the hollow wire.
Figure 13:
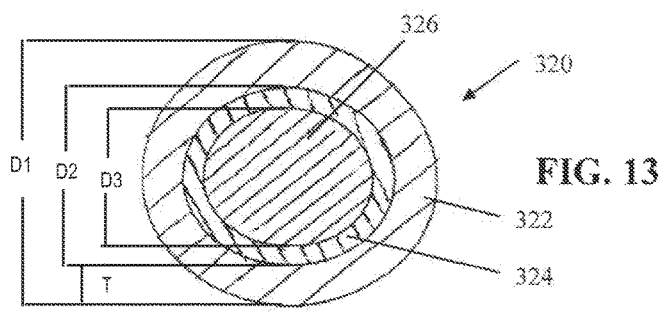
FIGS. 13-18 are cross-sectional and longitudinal cross-sectional views of the composite wire at various stages of the method of FIG. 12.
Figure 14:
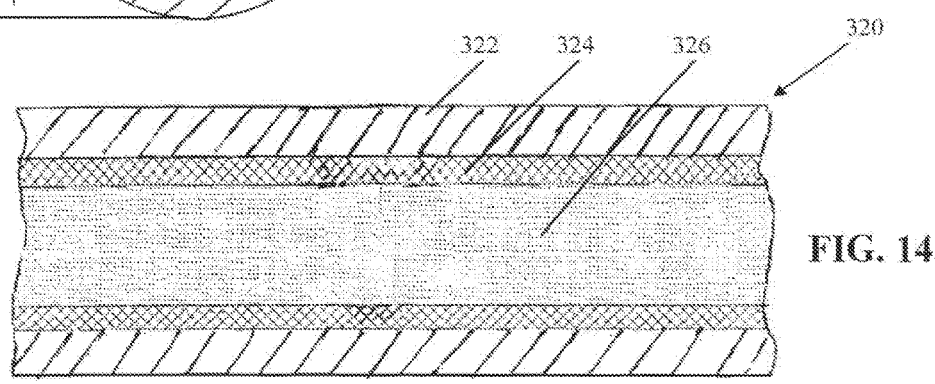

FIGS. 12-18 show a method for forming a hollow wire stent in accordance with an embodiment hereof. As shown in FIG. 12, step 400 is to utilize a composite wire 320 having an outer member 322, a radiopaque intermediate member 324, and a core member 326. Such a composite member 320 may be the same as composite member 120 shown in FIG. 4, simply replacing reference numerals 120, 122, 124, and 126 with reference numerals 320, 322, 324, and 326. Thus, FIG. 4 is not repeated here. A cross-section of such a composite member 320 is shown in FIG. 13 and a longitudinal cross-section of a portion of core wire 320 is shown in FIG. 14. Composite wire 320 may be formed by any method known in the art, for example and not by way of limitation, a co-drawing process, extrusion, cladding, or any other suitable method. Composite wire 320 may be formed by methods of forming composite wires known to those skilled in the art. Examples of composite wires and methods of forming composite wires can be found in U.S. Pat. No. 5,630,840 to Mayer, U.S. Pat. No. 6,248,190 to Stinson, U.S. Pat. No. 6,497,709 to Heath, and U.S. Pat. No. 7,101,392 to Heath, each of which is incorporated by reference herein in its entirety.

Outer member 322 may be any material that is suitable to be used as a stent, provided that it survives the process of removing core member 326, as described in more detail below. For example and not by way of limitation, outer member 322 may be a stainless steel, cobalt-chromium alloys, nickel-titanium alloys such as Nitinol, magnesium, or combinations thereof. The term "cobalt-chromium" alloys as used herein includes alloys with cobalt and chromium. Generally, materials such as, but not limited to, cobalt-nickel-chromium alloys ("MP35N" and "MP20N") and chromium-nickel-tungsten-cobalt alloys ("L605") and cobalt-chromium-nickel-molybdenum alloys ("ELGILOY") are the types of materials included in the term "cobalt-chromium alloys" as used herein. The requirements for the material of outer member 322 are that it be biocompatible, sufficiently resilient to be used as a stent, and that it survives the process for eliminating core member 326, as discussed in more detail below.

Intermediate member 324 is a radiopaque material. Further, intermediate member 324 is a material that is etched more slowly than core member 326 when exposed to the selected etchant, as described in more detail below. Accordingly, intermediate member 324 is more radiopaque that outer member 322 and is etched more slowly than core member 326 during the process of eliminating core member 326. Thus, selection of the material for intermediate member 324 depends on the material of core member 326 and the process selected for removing core member 326. Core member 326 is a sacrificial material that is removed without damaging outer member 322 and without completely removing intermediate member 324. In a non-limiting example, outer member 322 is made of MP35N, intermediate member 324 is made of tantalum, core member 326 is made of molybdenum, and the etching process to remove core member 326 is exposing core member 326 to xenon difluoride gas ($XeF_2$) gas at low pressure (1-6 Torr) and relatively high temperature (approximately 150° C.). Other examples of material combinations of outer member 322, intermediate member 324, core member 326, and the removal method are provided below in chart form.

A cross-section of composite wire 320 is shown in FIG. 13. Outer member 322 may have an outer diameter D1 in the range of 0.0017 inch to 0.016 inch and wall thickness T in the range of 0.0005 to 0.0025 inch, depending on the application, for example, in what lumen or organ and for what purpose the stent is to be utilized. Intermediate member 124 may have an inner diameter of about 0.0005 to 0.006 inch and a thickness of in the range of about 0.0001 to about 0.0025 inch. Core member 126 may have a diameter of about 0.0005 to about 0.006 inch. In one non-limiting example, core member 326 has a diameter of 0.001 inch, intermediate member 324 has a wall thickness of 0.0005 inch, and outer member 322 has a wall thickness of 0.00075 inch, resulting in an outer diameter D1 of core wire 320 0.0035 inch. The values listed above are merely examples and other diameters and thicknesses may be used depending on, for example, the materials used, the desired stent shape, and the purpose or location of the stent. Further, although the dimensions listed are described as diameters, other shapes of wire may be utilized and the values listed above can be converted to outer and inner dimensions.

Referring back to FIG. 12, step 410 is to shape the composite wire 320 into the stent pattern. As discussed above, the stent pattern can be the pattern shown in FIG. 8 or any other suitable pattern formed from a wire. Further, although the order of all the steps is not critical, step 410 should be done prior to removing core member 326, as explained in more detail below. However, the step of shaping the composite member 320 into the stent pattern does not have to include shaping composite member 320 into the final stent pattern. For example, and not by way of limitation, the step 410 of shaping the composite member 320 into a stent pattern may include only forming a waveform of struts 306 and crowns 308 in composite wire 320, with the step of helically wrapping the waveform into the final stent pattern occurring after the core member 326 has been removed. Shaping composite wire 320 into the stent pattern while core member 326 and intermediate member 324 are disposed within outer member 322 helps prevent kinking or other deformations from occurring in outer member 322 or intermediate member 324. Shaping the composite wire 320 into the stent pattern shown in FIG. 8 generally includes the steps of forming composite wire 320 into a two dimensional waveform pattern followed by wrapping the pattern around a mandrel, as known to those skilled in the art. The end result is a helical stent pattern formed onto a mandrel. Selected crowns 308 of the helical pattern may then be fused together and the stent may be removed from the mandrel. Step 410 of shaping composite wire 320 into the stent pattern can be performed with techniques known to those skilled in the art. For example, and not by way of limitation, forming the composite wire 320 into a two dimensional waveform can be achieved using techniques described in U.S. Application Publication Nos. 2010/0269950 to Hoff et al. and 2011/0070358 to Mauch et al., and co-pending U.S. application Ser. Nos. 13/191,134 and 13/190,775, filed Jul. 26, 2011, each of which is incorporated in its entirety by reference herein. Other techniques known to those skilled in the art could also be used.

Figure 15:
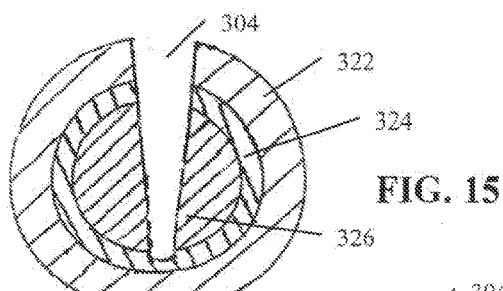
Figure 16:
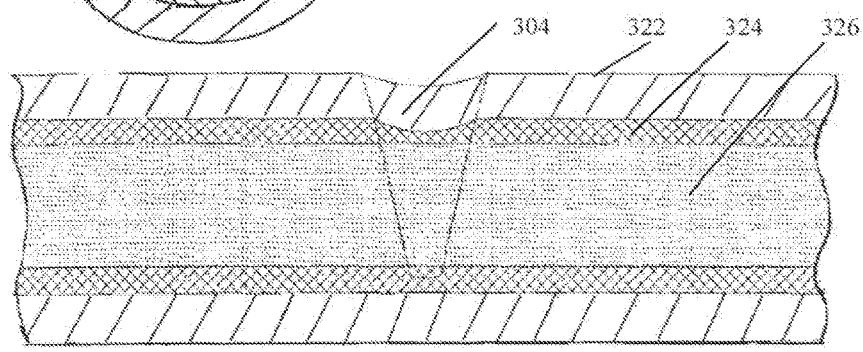
Figure 17:
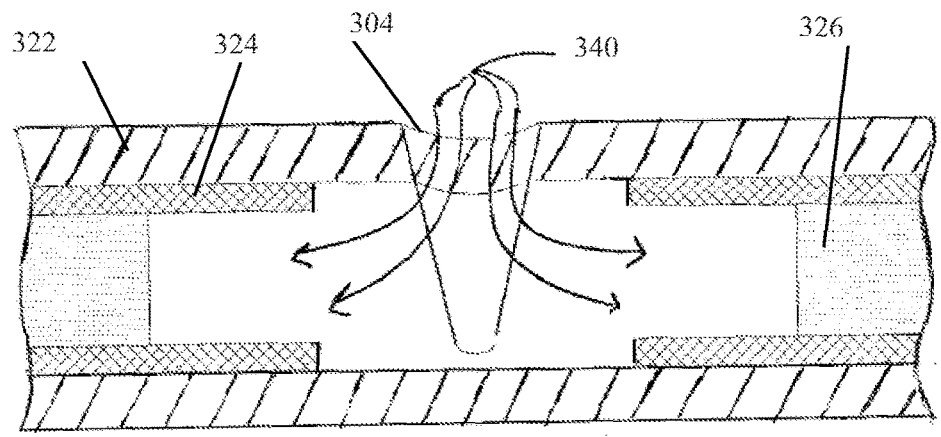
Figure 18:
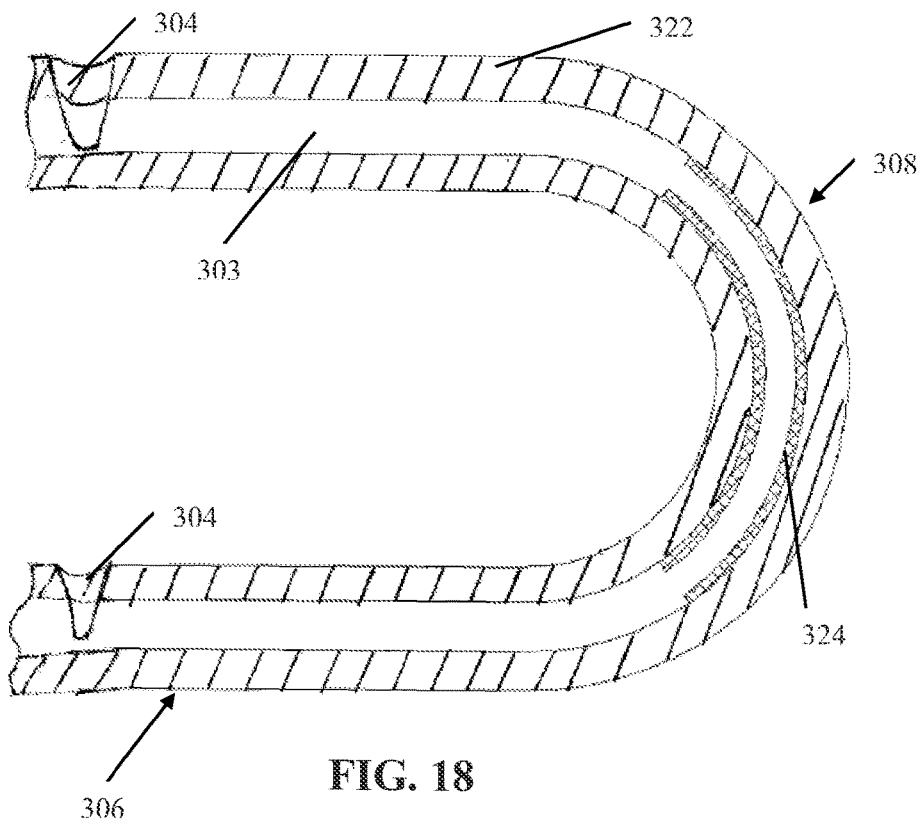

Step 420 shown in FIG. 12 is to provide openings 304 through outer member 322 and intermediate member 324. Openings 304 may be laser cut, drilled, etched, or otherwise provided through outer member 322 and intermediate member 324. Openings 304 may also be drilled partially or completely through core member 326 to provide better access to core member 326 by the etchant if openings 304 are provided prior to the step of removing core member 326, as described in more detail below. Step 420 need not be performed after step 410, nor before step 430, although it is preferred to be before step 430, as explained in more detail below. If step 420 is performed after step 410, a cross-section of composite wire 320 will include outer member 322, intermediate member 324, core member 326, and an opening 304, as shown in FIG. 15. Further, a longitudinal cross-section of core wire 320 with opening 304 is shown in FIG. 16.

Step 430 is to remove core member 326 and portions of intermediate member 324 from within outer member 322 without adversely affecting outer member 322, such as by chemical etching. Step 430 can be performed by any suitable process for removing core member 326 and removing portions of intermediate member 324, while preserving portions of intermediate member 324 and preserving outer member 322. In particular, in the example provided where radiopaque intermediate member 324 remains in the crowns 308 of stent 300, openings 304 may be provided through outer member 322 and intermediate member 324. In such an embodiment, the openings 304 may be provided only in the portions of composite wire 320 which will become the struts 306. The composite wire 320 is then exposed to an etchant (illustrated schematically by arrows 340 in FIG. 17) that removes core member 326 at a faster rate than the etchant removes intermediate member 324, as also illustrated schematically in FIG. 17. Core wire 320 is exposed to the etchant for sufficient time to completely eliminate core member 326 from struts 306 and crowns 308, although core member 326 may remain at ends 314, as described above. Because intermediate member 324 is removed at a slower rate than core member 326, intermediate member 324 is not removed from areas remote from the exposure point, openings 304 in this example, because the etchant does not have sufficient exposure time to etch these areas of intermediate member 324. In particular, exposing composite wire 320 formed from a outer member 322 of MP35N, an intermediate member 324 of tantalum, and a core member 326 of molybdenum to xenon difluoride ($XeF_2$) gas at low pressure (1-6 Torr) and relatively high temperature (approximately 150° C.) causes the xenon difluoride ($XeF_2$) to react with the molybdenum core member 326 at a faster rate than the tantalum intermediate member 324. By locating the openings 304 at mid-points of struts 306 and timing the exposure properly, core member 326 may be removed from the struts 306 and crowns 308, and intermediate member 324 may be removed from the struts 306, but not the crowns 308. If it is desired that the biologically or pharmacologically active substance 312 be eluted from the crowns 308 as well as the struts 306, openings 304 can be added to crowns 308 after removal of core member 326. Further, by varying the thickness of the different layers, exposure conditions, and other variables known to those skilled in the art, the amount and location of intermediate member 324 that remains can be controlled. If it is desired that only some of the crowns 308 include radiopaque intermediate member 324 and other crowns 308 do not include radiopaque intermediate member, openings 304 can be provided at the crowns 308 where it is desired that the intermediate member 324 be removed prior to exposure to the etchant. Thus, during removal of the core member 326, intermediate member 324 will also be removed. Intermediate member 324 may be maintained, for example and not by way of limitation, in every other crown, in crowns of every other winding, in crowns only at opposite ends of the stent, or other combinations desired by those of ordinary skill in the art.

Although a particular embodiment of an outer member 322 made from MP35N, an intermediate member 324 made from tantalum, a core member 326 made from molybdenum, and a xenon difluoride etchant has been described, those skilled in the art would recognize other combinations of materials and etchants that could be utilized. For example, and not by way of limitation, the combination of materials and etchants described in the chart below may be utilized.

| Etchant | Outer Member | Intermediate Member | Core Member |
| --- | --- | --- | --- |
| Xenon-difluoride | MP35N | tantalum | rhenium, molybdenum, tungsten, and alloys thereof. |

Further, other materials and methods for removing core members may be used, as described, for example, in U.S. Application Publication no. 2011/0008405 to Birdsall et al. and U.S. Application Publication No. 2011/0070358 to Mauch et al., each of which is incorporated by reference herein in its entirety.

Accordingly, after step 430 is completed, outer member 322 remains, intermediate member 324 has been removed from struts 306 but remains at crowns 308, core member 326 has been removed, and lumen 303 is formed in the interior of outer member 322 and intermediate member 324 where core member 326 and intermediate member 324 have been removed. This structure shown in partial longitudinal cross-section in FIG. 18. As noted above, openings 304 do not need to be formed prior to the step of removing core member 326 and partially removing intermediate member 324 as long as there is a way to expose core member 326 and intermediate member 324 to the etchant. For example, and not by way of limitation, temporary ports may for formed through outer member 322 and intermediate member 324 to expose core member 326 and intermediate member 324 to the etchant.

After core member 326 has been removed and intermediate member 324 has been partially removed, biologically or pharmacologically active substance 312 may be injected into lumen 303, as shown in step 440 of FIG. 12. This produces a hollow wire 302 with outer member 322, radiopaque intermediate member 324 lining an inside surface of outer member 322 at the crowns 308, biologically or pharmacologically active substance 312 filling lumen 303, and openings 304 through which biologically or pharmacologically active substance 312 may be eluted, as shown in FIGS. 9-11. Filling lumen 303 with a biologically or pharmacologically active substance may be accomplished by any means known to those skilled in the art. For example, and not by way of limitation, methods for filling lumens of hollow wires described in U.S. Application Publication No. 2011/0070357 to Mitchell et al., which is incorporated by reference herein in its entirety; and co-pending U.S. application Ser. Nos. 12/884,362; 12/884,451; 12/884,501; 12/884,578; 12/884,596 each filed on Sep. 17, 2010, and each of which is incorporated by reference herein in its entirety.

The biologically or pharmacologically active substance 312 may include, but is not limited to, the substances listed in this specification below, after description of FIGS. 23-33.

FIGS. 19-33 show an embodiment of a stent 500 and a method of making stent 500. In particular, stent 500 is formed from a hollow wire 502, wherein the hollow wire 502 is formed generally a hollow outer member with a lumen formed within the outer member. The term "wire" as used herein means an elongated element or filament or group of elongated elements or filaments and is not limited to a particular cross-sectional shape or material, unless so specified.

Figure 19:
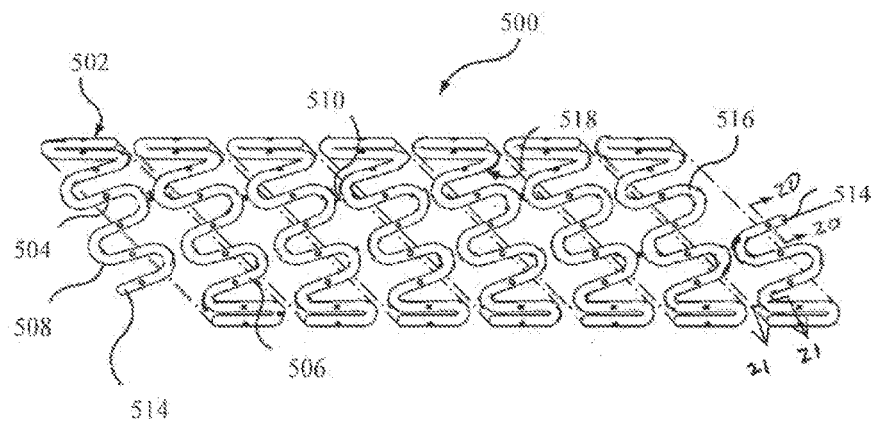
FIG. 19 is a schematic illustration of an exemplary stent in accordance with an embodiment hereof.

In the embodiment shown in FIG. 19, hollow wire 502 is formed into a series of generally sinusoidal waveforms including generally straight segments or struts 506 joined by bent segments or crowns 508 and the waveform is helically wound to form a generally tubular stent 500. In the embodiment shown in FIG. 19, selected crowns 508 of longitudinally adjacent sinusoids may be joined by, for example, fusion points 510. The invention hereof is not limited to the pattern shown in FIG. 19. Wire 502 of stent 500 can be formed into any pattern suitable for use as a stent. For example, and not by way of limitation, wire 502 of stent 500 can be formed into patterns disclosed in U.S. Pat. No. 4,800,882 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

Figure 20:
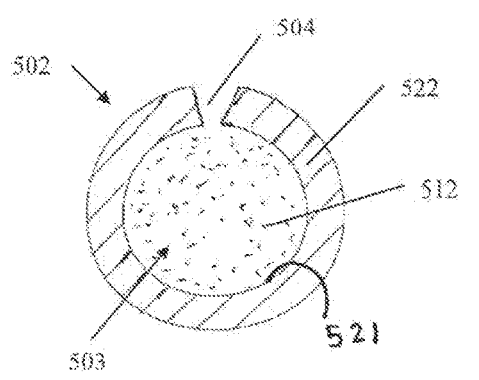
FIG. 20 is a cross-sectional view taken along line 20-20 of FIG. 19.
Figure 21:
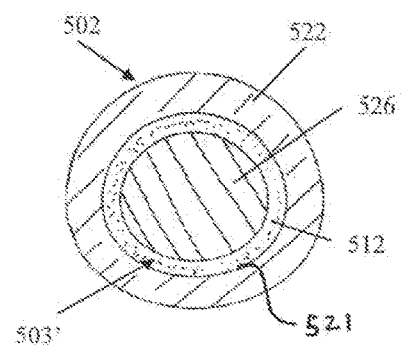
FIG. 21 is a cross-sectional view taken along line 21-21 of FIG. 19.
Figure 22:
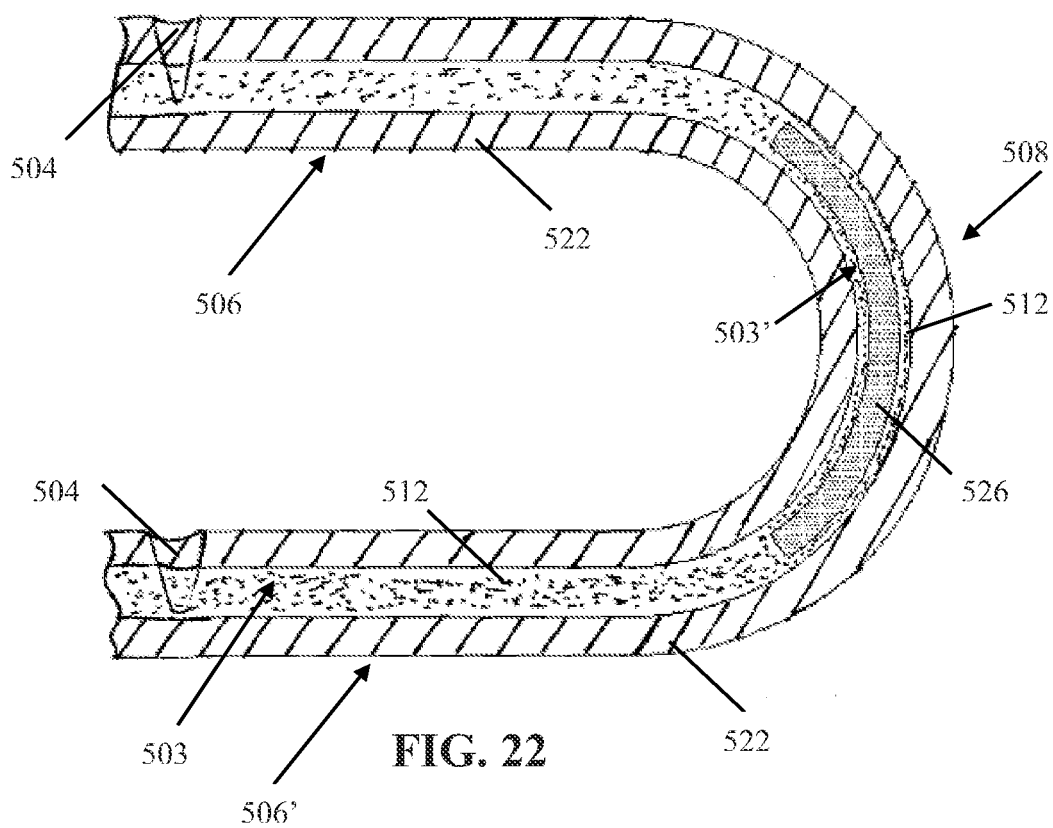
FIG. 22 is a partial longitudinal cross-section of a portion of the stent of FIG. 19.

As shown in FIGS. 20-22, hollow wire 502 of stent 500 includes different configurations for the struts 506 and the crowns 508. In particular, FIG. 20 shows a cross-section of wire 502 at struts 506. As can be seen in FIG. 20, wire 302 at struts 506 is formed from an outer member 522 with a lumen 503 filled with a biologically or pharmacologically active substance 512. Similarly, as shown in FIG. 21, wire 502 at crowns 508 is formed of a hollow outer member 522 having an inner diameter or inner dimension defined by an inner surface 521 of the outer member 522, a radiopaque core member 526 having an outer diameter or outer dimension smaller than the inner diameter/dimension of the outer member, and an annular lumen 503' disposed between an outer surface of radiopaque core member 526 and an inner surface of outer member 522. Lumen 503' is also filled with biologically or pharmacologically active substance 512. Lumens 503, 503' are in fluid communication with each other such that there is a continuous lumen from strut to adjacent crown to adjacent strut, as shown in the longitudinal cross-section of a portion of stent 500 shown in FIG. 22. FIG. 22 shows a longitudinal cross-section showing a portion of stent 500 including a strut 506, a crown 508, and a second strut 506', wherein a first end of crown 508 is attached to an end of strut 506 and a second end of crown 508 is attached to an end second strut 506'. In the embodiment shown, the attachment described is not an attachment of separate parts because wire 502 is continuous. However, stent 500 is not limited to a continuous wire stent. For example, and not by way of limitation, wires could be placed end to end, attached together, and then formed into stent 500 as described below. As shown in FIG. 22, radiopaque core member 526 is disposed within the interior of outer member 522 in the region of the crowns 508. The length of radiopaque core member 526 may be varied such that radiopaque core member 526 extends within outer member 522 for the entire crown 508, a portion of crown 508, or all of crown 508 and a portion of struts 506 adjoining crown 508, as described in more detail below. Radiopaque core member 526 should extend along crown 508 for at least a sufficient length such the radiopaque core member 526 is visible under fluoroscopic equipment. Every crown 508 of stent 500 may include radiopaque core member 526 or only some crowns 508 may include radiopaque intermediate member 526. Some options of how to select whether or not some crowns 508 include or do not include radiopaque intermediate member will be described below when describing the method of forming stent 500. Radiopaque core member 526 allows crowns 508 of stent 500 to be visible under X-ray or fluoroscopic imaging equipment when outer member 522, described below, is made of a material that has a radiopacity such that it has poor visibility or is difficult to visualize under X-ray or fluoroscopic imaging equipment. Thus, radiopaque core member 526 is more radiopaque than outer member 522. The term "radiopaque" refers to the ability of a substance to absorb X-rays. Few substances will transmit 100% of X-rays and few substances will absorb 100% of X-rays. For the purposes of this disclosure, radiopaque will refer to those substances or materials which have suitable visibility for stent procedures when being imaged by an X-ray imaging device such as but not limited to a fluoroscope.

Lumens 503, 503' allow for a biologically or pharmacologically active substance 512 to be deposited therewithin. Although hollow wire 502 is shown as generally having a circular cross-section, hollow wire 502 may be generally elliptical or rectangular in cross-section. Hollow wire 502 further includes cuts or openings 504 dispersed along its length to provide access to lumen 503 to permit biologically or pharmacologically active substance 512 to be released from lumen 503, 503'. Openings 504 may be disposed only on struts 506 of stent 500, only on crowns 508 of stent 500, or both struts 506 and crowns 508. Openings 504 may be sized and shaped as desired to control the elution rate of biologically or pharmacologically active substance 512 from stent 500. Larger sized openings 504 generally permit a faster elution rate and smaller sized openings 504 generally provide a slower elution rate. Further, the size and/or quantity of openings 504 may be varied along stent 500 in order to vary the quantity and/or rate of biologically or pharmacologically active substance 512 being eluted from stent 500 at different portions of stent 500. Openings 504 may be, for example and not by way of limitation, 5-30 µm in diameter. Openings 504 may be provided on an outwardly facing or abluminal surface 516 of stent 500, as shown in FIG. 19, or on the inwardly facing or luminal surface 518 of stent 500, or may be provided anywhere along the circumference of wire 502. Openings 504 may have a constant diameter through the depth or have a tapered or conical shape.

Ends 514 of wire 502 may be closed. Ends 514 may be closed by crimping excess material of wire 502 to close lumen 503. Ends 514 may also be closed by not removing intermediate member 524 and core member 526, described in more detail below, from the ends 514. Closing ends 514 prevents biologically or pharmacologically active substance 512 from prematurely releasing from ends 514. However, closing ends 514 is not required as substance 512 may be dried, provided within a polymer matrix, enclosed within a liner (not shown), or otherwise protected from premature release from ends 514. Further, ends 514 may be welded, crimped or otherwise connected to other portions of wire 502 such that the ends 514 are not free ends. Ends 514 may alternatively be provided as free ends.

Figure 23:
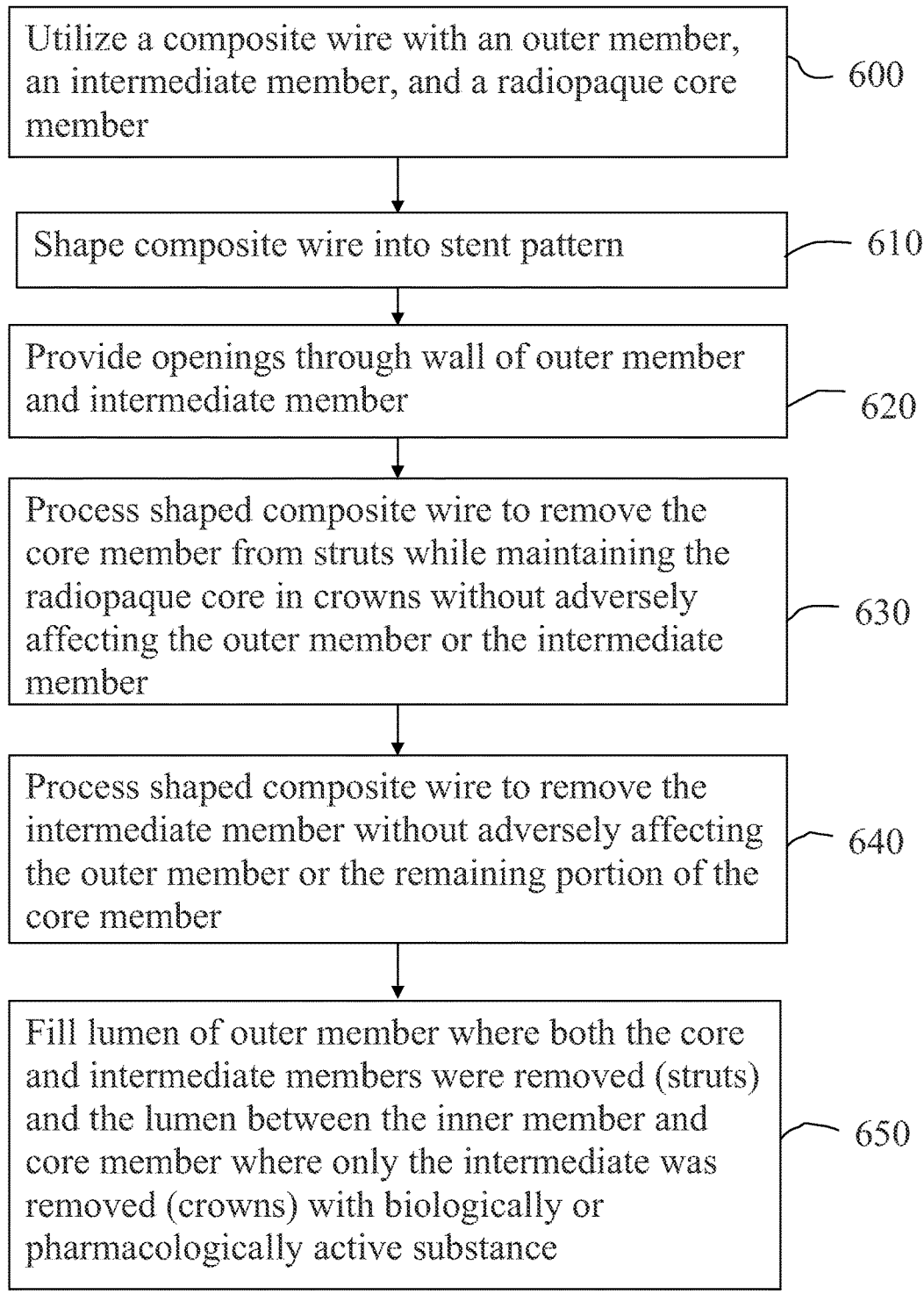
FIG. 23 is flow chart illustrating an embodiment of a method of forming a hollow wire stent including a radiopaque core member disposed at the crowns of the stent with a lumen between the core member and the outer member and a biologically or pharmacologically active substance disposed within the lumen of the outer member at the struts and in the lumen between the core member and the outer member at the crowns.
Figure 24:
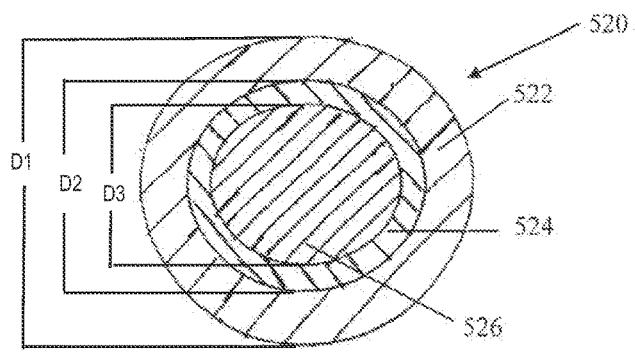

FIGS. 23-33 show a method for forming a hollow wire stent in accordance with an embodiment hereof. As shown in FIG. 23, step 600 is to utilize a composite wire 520 having an outer member 522, an intermediate member 524, and a radiopaque core member 526. Such a composite member 520 may be the same as composite member 120 shown in FIG. 4, simply replacing reference numerals 120, 122, 124, and 126 with reference numerals 520, 522, 524, and 526. Thus, FIG. 4 is not repeated here. A cross-section of such a composite member 520 is shown in FIG. 24. Composite wire 520 may be formed by any method known in the art, for example and not by way of limitation, a co-drawing process, extrusion, cladding, or any other suitable method. Composite wire 520 may be formed by methods of forming composite wires known to those skilled in the art. Examples of composite wires and methods of forming composite wires can be found in U.S. Pat. No. 5,630,840 to Mayer, U.S. Pat. No. 6,248,190 to Stinson, U.S. Pat. No. 6,497,709 to Heath, and U.S. Pat. No. 7,101,392 to Heath, each of which is incorporated by reference herein in its entirety.

Outer member 522 may be any material that is suitable to be used as a stent, provided that it survives the process of removing intermediate member 524 and portions of core member 526, as described in more detail below. For example and not by way of limitation, outer member 522 may be a stainless steel, cobalt-chromium alloys, nickel-titanium alloys such as Nitinol, magnesium, or combinations thereof. The term "cobalt-chromium" alloys as used herein includes alloys with cobalt and chromium. Generally, materials such as, but not limited to, cobalt-nickel-chromium alloys ("MP35N" and "MP20N") and chromium-nickel-tungsten-cobalt alloys ("L605") and cobalt-chromium-nickel-molybdenum alloys ("ELGILOY") are the types of materials included in the term "cobalt-chromium alloys" as used herein. The requirements for the material of outer member 522 are that it be biocompatible, sufficiently resilient to be used as a stent, and that it survives the process for eliminating intermediate member 524 and portions of core member 526, as discussed in more detail below.

Intermediate member 524 is a sacrificial material that is removed by a process that does not affect outer member 522 or core member 526. Intermediate member 524 has an outer diameter that is approximately equal to the inner diameter of hollow outer member 522. By "approximately equal" it is meant that the outer surface of intermediate member 524 is in contact with the inner surface of outer member 522. Core member 526 is a radiopaque material that is partially removed without damaging outer member 522. Core member 526 is more radiopaque than outer member 522. The selection of materials for outer member 522, intermediate member 524, and radiopaque core member 526 depends on the processes selected for partially removing the core member 526 and removing the intermediate member 524, as will be described in more detail below.

A cross-section of composite wire 520 is shown in FIG. 24. Outer member 522 may have an outer diameter D1 in the range of 0.0017 inch to 0.016 inch and wall thickness T in the range of 0.0005 to 0.0025 inch, depending on the application, for example, in what lumen or organ and for what purpose the stent is to be utilized. Intermediate member 124 may have an inner diameter of about 0.0005 to 0.006 inch and a thickness of in the range of about 0.0001 to about 0.0025 inch. Core member 126 may have a diameter of about 0.0005 to about 0.006 inch. In one non-limiting example, core member 526 has a diameter of 0.001 inch, intermediate member 524 has a wall thickness of 0.0005 inch, and outer member 522 has a wall thickness of 0.00075 inch, resulting in an outer diameter D1 of core wire 520 0.0035 inch. The values listed above are merely examples and other diameters and thicknesses may be used depending on, for example, the materials used, the desired stent shape, and the purpose or location of the stent. Further, although the composite wire has been shown and described as generally circular and dimensions have been referred to as inner and outer diameters, composite wire need not be circular and the inner and outer diameters may be referred to as inner and outer dimensions.

Referring back to FIG. 23, step 610 is to shape the composite wire 520 into the stent pattern. As discussed above, the stent pattern can be the pattern shown in FIG. 19 or any other suitable pattern formed from a wire. Further, although the order of all the steps is not critical, step 610 should be done prior to removing core member 526, as explained in more detail below. However, the step of shaping the composite member 520 into the stent pattern does not have to include shaping composite member 520 into the final stent pattern. For example, and not by way of limitation, the step 610 of shaping the composite member 520 into a stent pattern may include only forming a waveform of struts 506 and crowns 508 in composite wire 520, with the step of helically wrapping the waveform into the final stent pattern occurring after the core member 526 has been partially removed. Shaping composite wire 520 into the stent pattern while core member 526 and intermediate member 524 are disposed within outer member 522 helps prevent kinking or other deformations from occurring in outer member 522. Shaping the composite wire 520 into the stent pattern shown in FIG. 19 generally includes the steps of forming composite wire 520 into a two dimensional waveform pattern followed by wrapping the pattern around a mandrel, as known to those skilled in the art. The end result is a helical stent pattern formed onto a mandrel. Selected crowns 508 of the helical pattern may then be fused together and the stent may be removed from the mandrel. Step 610 of shaping composite wire 520 into the stent pattern can be performed with techniques known to those skilled in the art. For example, and not by way of limitation, forming the composite wire 520 into a two dimensional waveform can be achieved using techniques described in U.S. Application Publication Nos. 2010/0269950 to Hoff et al. and 2011/0070358 to Mauch et al., and co-pending U.S. application Ser. Nos. 13/191,134 and 13/190,775, filed Jul. 26, 2011, each of which is incorporated in its entirety by reference herein. Other techniques known to those skilled in the art could also be used.

Figure 25:
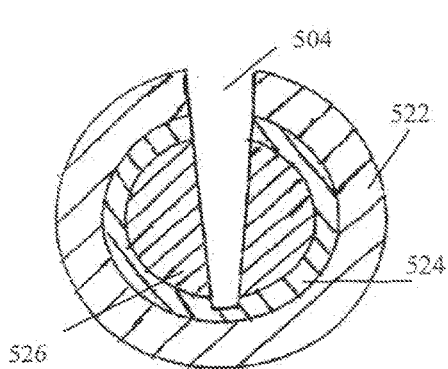
Figure 26:
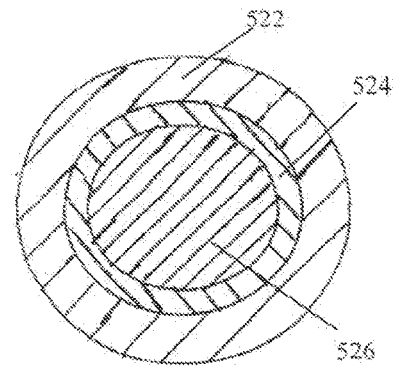

Step 620 shown in FIG. 23 is to provide openings 504 through outer member 522 and intermediate member 524. Openings 504 may be laser cut, drilled, etched, or otherwise provided through outer member 522 and intermediate member 524. Openings 504 may also be drilled partially or completely through core member 526 to provide better access to core member 526 by the etchant if openings 504 are provided prior to the step of partially removing core member 526, as described in more detail below. Step 620 need not be performed after step 610, nor before step 630, although it is preferred to be before step 630, as explained in more detail below. Further, openings 504 are preferably formed only in the strut regions 508 of stent 500 prior to step 630 such that core member 526 is not removed from crowns 508 during step 630. If step 620 is performed after step 610, a cross-section of composite wire 520 at the locations of openings 504 at struts 506 will include outer member 522, intermediate member 524, core member 526, and an opening 504, as shown in FIG. 25. Further, a cross-section after step 620 at crowns 508 will include outer member 522, intermediate member 524, and core member 526, without openings 504, as shown in FIG. 26.

Figure 27:
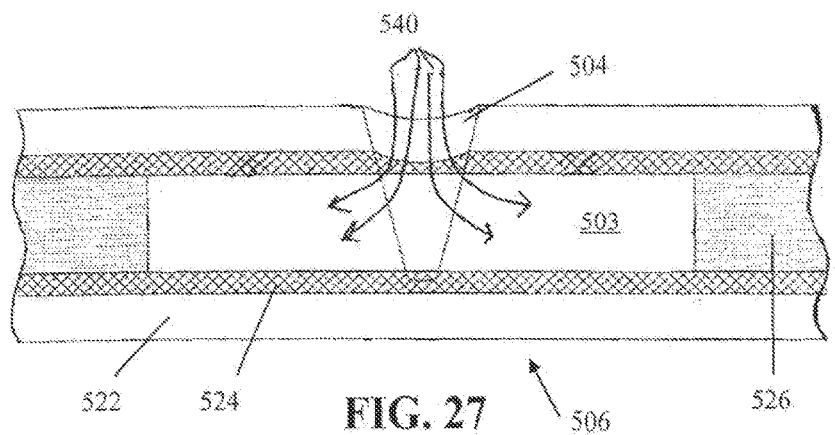

Step 630 is to partially remove core member 526 from within outer member 522 without adversely affecting outer member 522, such as by chemical etching. Step 630 can be performed by any suitable process for partially removing core member 526 while preserving outer member 522. In particular, in an example where outer member 522 is made from MP35N, intermediate member 524 is magnesium, zinc, copper, silver, and radiopaque core member 526 is made from tantalum, core member 526 may be partially removed by exposing core wire 520 to xenon difluoride ($XeF_2$) gas at low pressure (1-6 Torr) and relatively high temperature (approximately 150° C.), causing the xenon difluoride ($XeF_2$) to react with the tantalum core member 526 to form $TaF_5$ and Xe gases, which can be exhausted from lumen 503. By locating the openings 504 at mid-points of struts 506 and timing the exposure properly, core member 526 may be removed from the struts 506, but not from crowns 508, as explained, for example, in U.S. patent application Ser. No. 12/884,343 filed Sep. 17, 2010. FIG. 27 shows schematically a portion of a strut 506 being exposed to xenon difluoride ($XeF_2$) gas (shown schematically as arrows 540) to etch away core member 526. Upon completion of step 630, a cross-section of core wire 520 at an opening 504 through a strut region 506 of stent 500 is shown in FIG. 28, showing outer member 522, intermediate member 524, lumen 503, and opening 504. After step 630 a similar cross-section shown in FIG. 29 taken through a crown region 508 still includes outer member 522, intermediate member 524, and core member 526. FIG. 30 shows a longitudinal cross-section through a portion of shaped core wire 520 including a strut 506, crown 508, and a second strut 506' after step 630. As can be seen in FIG. 30, the strut regions 506 include outer member 522 and intermediate member 524, while the crown region 508 includes outer member 522, intermediate member 524, and core member 526.

Figure 31:
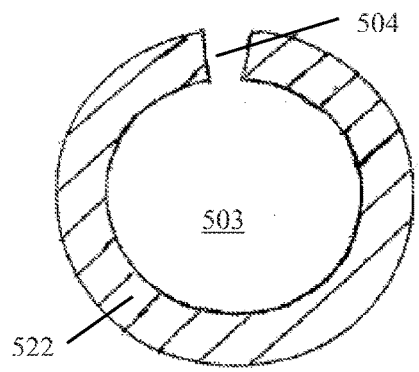
Figure 32:
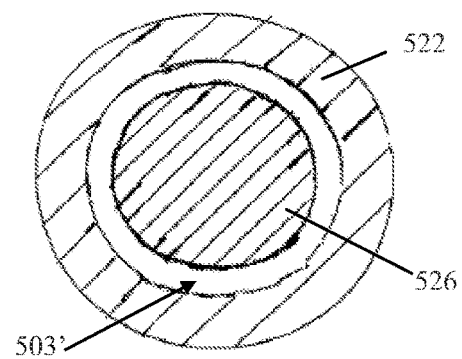
Figure 33:
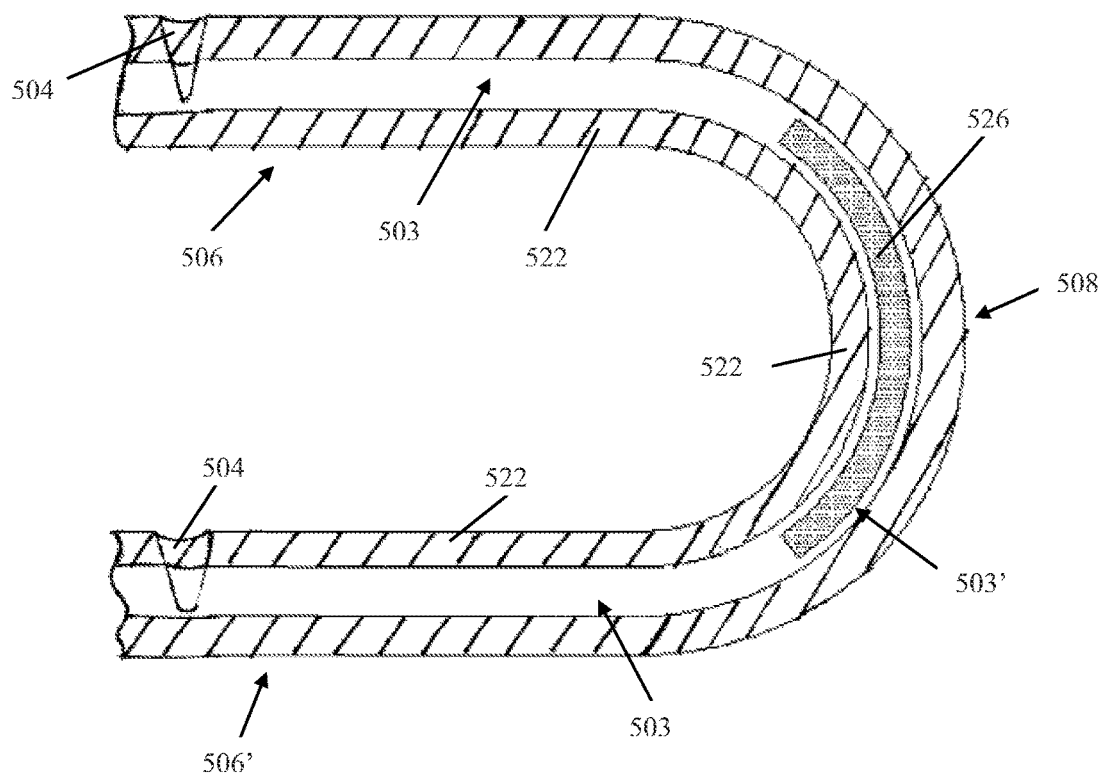

Referring back to FIG. 23, step 640 is to remove intermediate member 526 without damaging outer member 522 or the remaining portion of core member 526. For example, and not by way of limitation, intermediate member 524 may be removed by a wet etching process, such as nitric acid. In the example provided above, where outer member 522 is made from MP35N, intermediate member 524 is made from copper, and core member 526 is made from tantalum, a selective wet etch of nitric acid can be used to remove intermediate member 524. Upon completion of step 640, a cross-section of core wire 520 at an opening 504 through a strut region 506 of stent 500 is shown in FIG. 31, showing that intermediate member 524 has been removed, thus leaving outer member 522, lumen 503, and opening 504. After step 640 a similar cross-section shown in FIG. 32 taken through a crown region 508 also shows intermediate member 524 removed, leaving outer member 522, core member 526, and annular lumen 503' disposed between core member 526 and outer member 522. FIG. 33 shows a longitudinal cross-section through a portion of shaped core wire 520 including a strut 506, crown 508, and a second strut 506' after step 640. As can be seen in FIG. 33, the strut regions 506, 506' include outer member 522 and lumen 503, while the crown region 508 includes outer member 522, core member 526, and annular lumen 503' disposed between an outer surface of core member 526 and an inner surface of outer member 522. As also can be seen in FIG. 33, lumen 503 and annular lumen 503' are in fluid communication with each other.

Although a particular embodiment of an outer member 522 made from MP35N, an intermediate member 524 made from copper, a radiopaque core member 526 made from tantalum, xenon difluoride as the etchant to partially remove radiopaque core member 526, and a wet etch of nitric acid to etch remove intermediate member 524 has been described, those skilled in the art would recognize other combinations of materials and etchants that could be utilized. For example, and not by way of limitation, the combination of materials and etchants described in the chart below may be utilized.

| Outer Member | Intermediate Member | Intermediate Member Etchant | Core Member | Core Member Etchant |
|---|---|---|---|---|
| cobalt-chromium alloys (MP35N, MP20N, L605, ELGILOY) | Magnesium | Hydrochloric acid, most acids, salt water solution | Tantalum, tungsten, molybdenum, niobium, rhenium, Ta-2.5W | xenon-difluoride |
| Cobalt-chromium alloys (MP35N, MP20N, L605, ELGILOY) | Zinc | Hydrochloric, Nitric acid | | |
| Cobalt-chromium alloys (MP35N, MP20N, L605, ELGILOY) | Copper, silver | Nitric acid | | |
| Cobalt-chromium allows (MP35N, MP20N, L605, ELGILOY) | Gold | Potassium triiodide, cyanide solutions | | |
| cobalt-chromium alloys (MP35N, MP20N, L605, ELGILOY) | Tantalum, tungsten, molybdenum, niobium, rhenium, carbon, germanium, silicon, Ta-2.5W | xenon-difluoride | Gold | Potassium triiodide, cyanide solutions |

Further, other materials and methods for removing core members may be used, as described, for example, in U.S. Application Publication no. 2011/0008405 to Birdsall et al. and U.S. Application Publication No. 2011/0070358 to Mauch et al., each of which is incorporated by reference herein in its entirety.

Accordingly, after step 640 is completed, outer member 522 remains, intermediate member 524 has been removed, and core member has been removed from struts 506 but remains at crowns 508, leaving the structure shown in partial longitudinal cross-section in FIG. 33. As noted above, openings 504 do not need to be formed prior to the step of partially removing core member 526 and removing intermediate member 524 as long as there is a way to expose core member 526 and intermediate member 524 to the etchants. For example, and not by way of limitation, temporary ports may be formed through outer member 522 and intermediate member 524 to expose them to the etchants. Further, although it is explained above that in step 630 of partially removing core member 526 openings 504 are disposed only in strut regions 506, this does not mean that openings cannot be formed in crowns 508. If it is desired that the biologically or pharmacologically active substance 512 be eluted from the crowns 508 as well as the struts 506, openings 504 can be added to crowns 508 after partial removal of core member 526, or openings 504 can be formed prior to partial removal of core member 526 and the openings 504 can be masked off during exposure to the etchant so as not to remove core member 526 from the crowns 508. Further, although it has been disclosed that radiopaque core member 526 is removed from strut regions 506 and remains in crown regions 508, core member 526 does not need to remain at every crown 508. For example, and not by way of limitation, core member may remain only in every other crown, in one crown per winding, in all crowns for every other winding, in crowns at each end or only one end of the stent, or other combinations desired by those skilled in the art based upon the teachings of this disclosure. Some such methods and combinations are explained in U.S. application Ser. No. 12/884,343 filed Sep. 17, 2010, which is incorporated by reference herein in its entirety.

After core member 526 has been partially removed and intermediate member 524 has been removed, biologically or pharmacologically active substance 512 may be injected into lumen 503, 503', as shown in step 650 of FIG. 23. This produces a hollow wire 502 with outer member 522, radiopaque core member 526 at crowns 508, biologically or pharmacologically active substance 512 filling lumen 503 in struts 506 and lumen 503' at crowns 508, and openings 504 through which biologically or pharmacologically active substance 512 may be eluted, as shown in FIGS. 20-22. Filling lumen 503, 503' with a biologically or pharmacologically active substance may be accomplished by any means known to those skilled in the art. For example, and not by way of limitation, methods for filling lumens of hollow wires described in U.S. Application Publication No. 2011/0070357 to Mitchell et al., which is incorporated by reference herein in its entirety; and co-pending U.S. application Ser. Nos. 12/884,362; 12/884,451; 12/884,501; 12/884,578; 12/884,596 each filed on Sep. 17, 2010, and each of which is incorporated by reference herein in its entirety.

The biologically or pharmacologically active substance 512 may include, but is not limited to, the substances listed in this specification below.

Those of ordinary skill in the art would recognize that the methods described with respect FIGS. 12 and 23 to make the stents shown and described with respect to FIGS. 8-11 and 19-22, respectively, may be reversed/modified such that the method of FIG. 12 can produce the stent of FIGS. 19-22 and the method of FIG. 23 can produce the stent of FIGS. 8-11. For example, relying on the method of FIG. 12, the intermediate member may be selected to etch faster than a radiopaque core member. Thus, when exposed to an etchant, such as xenon difluoride, the exposure can be timed such that the intermediate member is completely removed and the radiopaque core member is removed from the struts, but not the crowns. After filling the lumen with a biologically or pharmacologically active substance, the method results in the stent shown and described with respect to FIGS. 19-22. Similarly, the method described with respect to FIG. 23 can be used to produce the stent described with respect to FIGS. 8-11. In particular, a dry etch such as xenon difluoride gas can be used to remove the core member, and a wet etch can subsequently be used to remove radiopaque intermediate member from the strut regions and not remove radiopaque intermediate member from the crown regions. After filling the lumen with a biologically or pharmacologically active substance, the method results in the stent shown and described with respect to FIGS. 8-11. Those skilled in the art would be capable of making the necessary adjustments in the methods, such as but not limited to materials used and timing of the steps, to produce the desired stent.

The biologically or pharmacologically active substance 112, 312, 512 may include, but are not limited to, biologoicantineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include ABT-578 (a synthetic analog of rapamycin), rapamycin (sirolimus), zotarolimus, everolimus, angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other biologically or pharmacologically active substances or agents that may be used include nitric oxide, alpha-interferon, genetically engineered epithelial cells, and dexamethasone. In other examples, the biologically or pharmacologically active substance is a radioactive isotope for implantable device usage in radiotherapeutic procedures. Examples of radioactive isotopes include, but are not limited to, phosphorus ($P^{32}$), palladium ($Pd^{103}$), cesium ($Cs^{131}$), Iridium ($I^{192}$) and iodine ($I^{125}$). While the preventative and treatment properties of the foregoing biologically or pharmacologically active substances are well-known to those of ordinary skill in the art, the biologically or pharmacologically active substances are provided by way of example and are not meant to be limiting. Other biologically or pharmacologically active substances are equally applicable for use with the disclosed methods and compositions.

Further, a carrier may be used with the biologically or pharmacologically active substance. Examples of suitable carriers include, but are not limited to, ethanol, acetone, tetrahydrofuran, dymethylsulfoxide, a combination thereof, or other suitable carriers known to those skilled in the art. Still further, a surfactant may be formulated with the biologically or pharmacologically active substance and the solvent to aid elution of the biologically or pharmacologically active substance.

Stents 100, 300, 500 may be used conventionally in blood vessels of the body to support such a vessel after an angioplasty procedure. It is known that certain biologically or pharmacologically active substances eluted from stents may prevent restenosis or other complications associated with angioplasty or stents. Stents 100, 300, 500 may alternatively be used in other organs or tissues of the body for delivery of biologically or pharmacologically active substance to treat tumors, inflammation, nervous conditions, or other conditions that would be apparent to those skilled in the art.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A method of forming a stent comprising the steps of:
   shaping a composite wire into a stent pattern, wherein the composite wire comprises an outer member, a radiopaque intermediate member, and a core member, wherein the radiopaque intermediate member is disposed between the outer member and the core member;
   processing the composite wire such that the core member is removed without adversely affecting the outer member, thereby leaving an outer member, the radiopaque intermediate member lining at least a portion of an inner surface of the outer member, and a lumen, at least a portion of the lumen defined by an inner surface of the radiopaque intermediate member;
   filling at least a portion of the lumen with a biologically or pharmacologically active substance; and
   providing openings through at least the outer member such that the openings extend from an outer surface of the outer member to the lumen.

2. The method of claim 1, wherein the step of processing the composite wire such that the core member is removed also comprises removing portions of the radiopaque intermediate member such that portions of the inner surface of the outer member are not lined with the radiopaque intermediate member.

3. The method of claim 2, wherein the step of shaping the composite wire into a stent form includes shaping the composite wire into a waveform including struts connected by crowns, and wherein after the step of processing the composite wire to remove the core member and portions of the radiopaque intermediate member, the radiopaque intermediate member lines the inner surface of the outer member only in crowns of the waveform.

4. The method of claim 1, wherein the biologically or pharmacologically active substance is selected from the group consisting of antineoplastic, antimitotic, antiinflammatory, antiplatelet, anticoagulant, anti fibrin, antithrombin, antiproliferative, antibiotic, antioxidant, and antiallergic substances as well as combinations thereof.

5. The method of claim 1, wherein the step of providing openings through the outer member comprises laser drilling openings through the outer member and the intermediate member.

6. The method of claim 1, wherein the step of providing openings through the outer member occurs before the step of processing the composite wire to remove the core member.

7. The method of claim 1, wherein the outer member comprises a cobalt-chromium alloy, the radiopaque intermediate member comprises a platinum-iridium alloy, the core member is selected from the group consisting of tantalum, tungsten, molybdenum, niobium, rhenium, carbon, germanium, silicon, and tantalum-tungsten alloys, and the step of removing the core member comprises exposing the core member to xenon-difluoride.

8. The method of claim 1, wherein the outer member comprises a cobalt-chromium alloy, the radiopaque intermediate member is selected from the group consisting of tantalum and tantalum-tungsten alloys, the core member comprises copper or silver, and the step of removing the core member comprises exposing the core member to nitric acid.

9. The method of claim 1, wherein the outer member comprises a cobalt-chromium alloy, the radiopaque intermediate member is selected from the group consisting of platinum-iridium alloys, tantalum, and tantalum-tungsten alloys, the core member is selected from the group consisting of zinc and magnesium, and the step of removing the core member comprises exposing the core member to water or salt water or heat to melt or sublimate the core member.

10. The method of claim 2, wherein the outer member comprises a cobalt-nickel-chromium-molybdenum alloy, the radiopaque intermediate member comprises tantalum, the core member is selected from the group consisting of rhenium, molybdenum, tungsten, and alloys thereof, and the step of removing the core member and portions of the radiopaque intermediate member comprises exposing the core member to xenon-difluoride such that the core member is etched at a faster rate than the radiopaque intermediate member.

11. The method of claim 1, further comprising the step of removing portions of the intermediate member in a separate step from the step of removing the core member.

12. The method of claim 11, wherein the step of removing the core member is a dry etch process and the step of removing portions of the radiopaque intermediate member is a selective wet etch process.

* * * * *